US 10,721,936 B2
Jul. 28, 2020

(12) United States Patent
White, Jr. et al.

(54) COMPOSITIONS AND METHODS COMPRISING ENDOPHYTIC BACTERIUM FOR APPLICATION TO GRASSES TO INCREASE PLANT GROWTH, SUPPRESS SOIL BORNE FUNGAL DISEASES, AND REDUCE VIGOR OF WEEDY COMPETITORS

(71) Applicants: Rutgers, The State University of New Jersey, New Brunswick, NJ (US); UNITED STATES GEOLOGICAL SURVEY, Reston, VA (US)

(72) Inventors: James F. White, Jr., South River, NJ (US); Kurt P. Kowalski, Ann Arbor, MI (US); Kathryn Kingsley, Robbinsville, NJ (US)

(73) Assignees: Rutgers, The State University of NJ, New Brunswick, NJ (US); United States Geological Survey, Reston, VA (US)

(*) Notice: Subject to any disclaimer, the term of this patent is extended or adjusted under 35 U.S.C. 154(b) by 0 days.

(21) Appl. No.: 15/657,100

(22) Filed: Jul. 21, 2017

(65) Prior Publication Data

US 2018/0020672 A1    Jan. 25, 2018

Related U.S. Application Data

(63) Continuation-in-part of application No. PCT/US2016/043408, filed on Jul. 21, 2016.

(51) Int. Cl.
| | | |
|---|---|---|
| *A01N 63/00* | (2020.01) | |
| *C12N 1/20* | (2006.01) | |
| *C12R 1/39* | (2006.01) | |
| *C12R 1/38* | (2006.01) | |
| *C12R 1/01* | (2006.01) | |

(52) U.S. Cl.
CPC ............ *A01N 63/00* (2013.01); *C12N 1/20* (2013.01); *C12R 1/01* (2013.01); *C12R 1/38* (2013.01); *C12R 1/39* (2013.01)

(58) Field of Classification Search
CPC .................................................. A01N 63/00
USPC ........................................................ 800/298
See application file for complete search history.

(56) References Cited

U.S. PATENT DOCUMENTS

| | | |
|---|---|---|
| 2009/0324564 A1 | 12/2009 | Maeda |
| 2013/0031673 A1 | 1/2013 | Grandlic et al. |
| 2015/0373993 A1* | 12/2015 | von Maltzahn ........ A01N 63/02 800/300.1 |
| 2016/0316760 A1 | 11/2016 | Ambrose et al. |
| 2017/0020138 A1 | 1/2017 | Von Maltzahn et al. |
| 2017/0238552 A1 | 8/2017 | Raizada et al. |
| 2018/0020672 A1 | 1/2018 | White, Jr. et al. |

FOREIGN PATENT DOCUMENTS

WO    2016044954 A1    3/2016

OTHER PUBLICATIONS

Gond, Surendra K. et al., "Effect of bacterial endophyte on expression of defense genes in Indian popcorn against Fusarium moiliforme", Symbiosis, 66: 133-140 (2015).
Ligon, James M. et al., "Natural products with antifungal activity from Pseudomonas biocontrol bacteria", Pest Manag. Sci., 56: 688-695 (2000).
Mandal, Santi M. et al., "Isolation and characterization of diverse antimicrobial lipopeptides produced by Citrobacter and Enterobacter", BMC Microbiology, 13: 152 (2013).
Rodriguez, Rusty J. et al., "Stress tolerance in plants via habitat-adapted symbiosis", The ISME Journal, 2: 404-416 (2008).
Soares, M.A. et al., "Functional Role of Bacteria from Invasive Phragmites australis in Promotion of Host Growth", Microb. Ecol., 72: 407-417 (2016).
Soares, Marcos Antonio et al., "Evalouation of the functional roles of fungal endophytes of Phragmites australios from high saline and low saline habitats", Biol. Invasions, 18: 2689-2702 (2016).
Spence, Carla et al.. BMC Plant Biology, "Natural rice rhizospheric microbes suppress rice blast infections", 14: 130 (2014).
White, James F. et al., "A proposed mechanism for nitrogen acquhisition byh grass seedlings through oxidation f symbiotic bacteria", Symbiosis, 57: 61-71 (2012).
White, James F. et al., "Collaboration between grass seedlings and rhizobacteria to scavenge organic nitrogen in soils", AoB Plants, DOI: 10.1093/aobpla/plu093 (Jan. 2015).
Zeller, Simon L. et al., "Host-Plant Selectivity of Rhizobacteria in a Crop/Weed Model System", PLoS ONE, 2(9): e846.DOI:10.137I/joumal.pone.0000846 (2007).
White, James F. et al., "Collaboration between grass seedlings and rhizobacteria to scavenge organic nitrogen in soils", AoB Plants, 7: 1-11 (2015).
White, James F. et al., How Do Endophytes Function to Enhance Host Plant Growth and Survival?, AACC International. The Future of Food Sustainability and Safety Symposium. Presentation. May 2016; pp. 1-93.
"KYO74468: Pseudomonas syringae strain BAV3981 16S ribosomal RNA gene, partial sequence", NCBI GenBank, Accession No. KY074468, Dec. 20, 2016.
"AB109886: Pseudomonas graminis Gene for 16S rRNA, Partial Sequence, Strain: KF701", NC BI Genbank, Accession No. AB109886, Jul. 29, 2009.

(Continued)

*Primary Examiner* — Li Zheng
(74) *Attorney, Agent, or Firm* — Kathleen D. Rigaut; Howson & Howson LLP

(57) ABSTRACT

Endophytic bacteria, compositions comprising the same, and methods of use thereof are disclosed which increase the root and shoot growth of grass hosts, suppress growth of soil borne fungal pathogens of host plants, increase resistance of the grass to diseases and reduce competitiveness of distantly related competitor weeds of the crop.

22 Claims, 24 Drawing Sheets

Specification includes a Sequence Listing.

(56) References Cited

OTHER PUBLICATIONS

"JF901350: Endophytic bacterium 4P-2 16S ribosomal RNA gene, partial sequence", NCBI GenBank, Accession No. JP901350, Dec. 7, 2012.

"AY753173: Enterobacter endosymbiont of Metaseiulus occidentalis clone pAJ240 16S ribosomal RNA gene, partial sequence", NCBI GenBank, Accession No. AY753173, Sep. 21, 2018.

"HQ538790: *Pseudomonas* sp. M47tronco1 16S ribosomal RNA gene, partial sequence", NCBI GenBank, Accession No. HQ538790, May 2, 2012.

"KP860310: Microbacterium oxydans strain B2 16S ribosomal RNA gene, partial sequence", NCBI GenBank, Accession No. KP860310, Jun. 8, 2016.

Proenca et al., "Diversity of Bacteria Associated with Bursaphelenchus xylophilus and Other Nematodes Isolated from Pinus pinaster Trees with Pine Wilt Disease", PLoS One, 5(1): e15192, pp. 1-9 (2010).

Rodriguez et al., "{Fungal endophytes: diversity and functional roles", New Phytologist, 182(2): 314-330 (2009).

International Search Report and Written Opinion, dated Oct. 4, 2018, issued in corresponding International Application No. PCT/US2018/43259, filed Jul. 23, 2018.

International Search Report and Written Opinion, dated Oct. 19, 2016, issued in corresponding International Application No. PCT/US2016/43408, filed Jul. 21, 2016.

\* cited by examiner

SEQUENCE LISTING

```
<160> NUMBER OF SEQ ID NOS: 16

<210> SEQ ID NO 1
<211> LENGTH: 667
<212> TYPE: DNA
<213> ORGANISM: Pseudomonas fluorescens

<400> SEQUENCE: 1
tagataccct ggtagtccac gccgtaacga tgtcaactag ccgttgggag ccttgagctc      60
ttagtggcgc agctaacgca ttaagttgac cgcctgggga gtacggccgc aaggttaaaa     120
ctcaaatgaa ttgacggggg cccgcacaag cggtggagca tgtggtttaa ttcgaagcaa     180
cgcgaagaac cttaccaggc cttgacatcc aatgaacttt ctagagatag attggtgcct     240
tcgggaacat tgagacaggt gctgcatggc tgtcgtcagc tcgtgtcgtg agatgttggg     300
```

```
ttaagtcccg taacgagcgc aacccttgtc cttagttacc agcacgttat ggtgggcact    360
ctaaggagac tgccggtgac aaaccggagg aaggtgggga tgacgtcaag tcatcatggc    420
ccttacggcc tgggctacac acgtgctaca atggtcggta caaagggttg ccaagccgcg    480
aggtggagct aatcccataa aaccgatcgt agtccggatc gcagtctgca actcgactgc    540
gtgaagtcgg aatcgctagt aatcgcgaat cagaatgtcg cggtgaatac gttcccgggc    600
cttgtacaca ccgcccgtca caccatggga gtgggttgca ccagaagtag ctagtttaac    660
cttcggg                                                              667

<210> SEQ ID NO 2
<211> LENGTH: 322
<212> TYPE: DNA
<213> ORGANISM: Pseudomonas sp.

<400> SEQUENCE: 2
gtccttagtt accagcacgt tatggtgggc actctaagga gactgccggt gacaaaccgg     60
aggaaggtgg ggatgacgtc aagtcatcat ggcccttacg gcctgggcta cacacgtgct    120
acaatggtcg gtacagaggg ttgccaagcc gcgaggtgga gctaatctca caaaaccgat    180
cgtagtccgg atcgcagtct gcaactcgac tgcgtgaagt cggaatcgct agtaatcgcg    240
aatcagaatg tcgcggtgaa tacgttcccg ggccttgtac acaccgcccg tcacaccatg    300
ggagtgggtt gcaccagaag ta                                             322

<210> SEQ ID NO 3
<211> LENGTH: 283
<212> TYPE: DNA
<213> ORGANISM: Pseudomonas sp.

<400> SEQUENCE: 3
ctacttctgg tgcaacccac tcccatggtg tgacgggcgg tgtgtacaag gcccgggaac     60
gtattcaccg cgacattctg attgcgatt actagcgatt ccgacttcac gcagtcgagt    120
tgcagactgc gatccggact acgatcggtt ttgtgagatt agctccacct cgcggcttgg    180
caaccctctg taccgaccat tgtagcacgt gtgtagccca ggccgtaagg gccatgatga    240
cttgacgtca tccccacctt cctccggttt gtcaccggca gtc                      283

<210> SEQ ID NO 4
<211> LENGTH: 544
<212> TYPE: DNA
<213> ORGANISM: Pseudomonas sp.

<400> SEQUENCE: 4
tttgacgtta ccgacagaat aagcaccggc taactctgtg ccagcagccg cggtaataca     60
gagggtgcaa gcgttaatcg gaattactgg gcgtaaagcg cgcgtaggtg gtttgttaag    120
ttggatgtga aagcccccgg gctcaacctg gaactgcatc caaaactggc aagctagagt    180
acggtagagg gtggtggaat ttcctgtgta gcggtgaaat gcgtagatat aggaaggaac    240
accagtggcg aaggcgacca cctggactga tactgacact gaggtgcgaa agcgtgggga    300
gcaaacagga ttagataccc tggtagtcca cgccgtaacg atgtcaacta gccgttggaa    360
tccttgagat tttagtggcg cagctaacgc attaagttga ccgcctgggg agtacggccg    420
caaggttaaa actcaaatga attgacgggg gcccgcacaa gcggtggagc atgtggttta    480
attcgaagca acgcgaagaa ccttaccggc cttgacatgc agagaacttt ccagagatgg    540
```

```
                                  atgg                                               544

<210> SEQ ID NO 5
<211> LENGTH: 812
<212> TYPE: DNA
<213> ORGANISM: Pseudomonas sp.

<400> SEQUENCE: 5
tgggaactgc atccaaaact ggcaagctag agtacggtag agggtggtgg aatttcctgt        60
gtagcggtga aatgcgtaga tataggaagg aacaccagtg gcgaaggcga ccacctggac       120
tgatactgac actgaggtgc gaaagcgtgg ggagcaaaca ggattagata ccctggtagt       180
ccacgccgta aacgatgtca actagccgtt ggaatccttg agattttagt ggcgcagcta       240
acgcattaag ttgaccgcct ggggagtacg gccgcaaggt taaaactcaa atgaattgac       300
gggggcccgc acaagcggtg gagcatgtgg tttaattcga agcaacgcga agaaccttac       360
caggccttga catgcagaga actttccaga gatggattgg tgccttcggg aactctgaca       420
caggtgctgc atggctgtcg tcagctcgtg tcgtgagatg ttgggttaag tcccgtaacg       480
agcgcaaccc ttgtccttag ttaccagcac gttatggtgg gcactctaag gagactgccg       540
gtgacaaacc ggaggaaggt ggggatgacg tcaagtcatc atggccctta cggcctgggc       600
tacacacgtg ctacaatggt cggtacagag ggttgccaag ccgcgaggtg gagctaatct       660
cacaaaaccg atcgtagtcc ggatcgcagt ctgcaactcg actgcgtgaa gtcggaatcg       720
ctagtaatcg cgaatcagaa tgtcgcggtg aatacgttcc cgggccttgt acacaccgcc       780
cgtcacacca tgggagtggg ttgcaccaga ag                                     812

<210> SEQ ID NO 6
<211> LENGTH: 372
<212> TYPE: DNA
<213> ORGANISM: Pantoea sp.

<400> SEQUENCE: 6
aagctcgtgt tgtgaaatgt tgggttaagt cccgcaacga gcgcaaccct tatcctttgt        60
tgccagcgat tcggtcggga actcaaagga gactgccggt gataaaccgg aggaaggtgg       120
ggatgacgtc aagtcatcat ggcccttacg agtagggcta cacacgtgct acaatggcgc       180
atacaaagag aagcgacctc gcgagagcaa gcggacctca caaagtgcgt cgtagtccgg       240
atcggagtct gcaactcgac tccgtgaagt cggaatcgct agtaatcgtg gatcagaatg       300
ccacggtgaa tacgttcccg ggccttgtac acaccgcccg tcacaccatg ggagtgggtt       360
gcaaaagaag ta                                                           372

<210> SEQ ID NO 7
<211> LENGTH: 697
<212> TYPE: DNA
<213> ORGANISM: Pseudomonas sp.

<400> SEQUENCE: 7
gaaggttaga ctagctactt ctggtgcaac ccactcccat ggtgtgacgg gcggtgtgta        60
caaggcccgg gaacgtattc accgcgacat tctgattcgc gattactagc gattccgact       120
tcacgcagtc gagttgcaga ctgcgatccg gactacgatc ggttttgtgg gattagctcc       180
acctcgcggc ttggcaaccc tctgtaccga ccattgtagc acgtgtgtag cccaggccgt       240
aagggccatg atgacttgac gtcatcccca ccttcctccg gtttgtcacc ggcagtctcc       300
ttagagtgcc caccatcacg tgctggtaac taaggacaag ggttgcgctc gttacgggac       360
```

```
ttaacccaac atctcacgac acgagctgac gacagccatg cagcacctgt ctcaatgttc      420
ccgaaggcac caatccatct ctggaaagtt cattggatgt caaggcctgg taaggttctt      480
cgcgttgctt cgaattaaac cacatgctcc accgcttgtg cgggccccg tcaattcatt       540 tgagttttaa ccttgcggcc gtactcccca ggcggtcaac ttaatgcgtt agctgcgcca      600
ctaagagctc aaggctccca acggctagtt gacatcgttt acggcgtgga ctaccagggt      660
atctaatcct gtttgctccc cacgctttcg cacctca                               697

<210> SEQ ID NO 8
<211> LENGTH: 287
<212> TYPE: DNA
<213> ORGANISM: Pseudomonas sp.

<400> SEQUENCE: 8
cttctggtgc aacccactcc catggtgtga cgggcggtgt gtacaaggcc cggaacgta       60 ttcaccgcga cattctgatt cgcgattact agcgattccg acttcacgca gtcgagttgc     120
agactgcgat ccggactacg atcggttttg tgggattagc tccacctcgc ggcttggcaa     180
ccctctgtac cgaccattgt agcacgtgtg tagcccaggc cgtaagggcc atgatgactt     240
gacgtcatcc ccaccttcct ccggtttgtc accggcagtc tccttag                   287

<210> SEQ ID NO 9
<211> LENGTH: 814
<212> TYPE: DNA
<213> ORGANISM: Pseudomonas sp.

<400> SEQUENCE: 9
taccgtcccc ccgaaggtta gactagctac ttctggtgca acccactccc atggtgtgac      60
gggcggtgtg tacaaggccc ggaacgtat tcaccgcgac attctgattc gcgattacta      120
gcgattccga cttcacgcag tcgagttgca gactgcgatc cggactacga tcggttttat    180
gggattagct ccacctcgcg gcttggcaac cctctgtacc gaccattgta gcacgtgtgt    240
agcccaggcc gtaagggcca tgatgacttg acgtcatccc caccttcctc cggtttgtca    300
ccggcagtct ccttagagtg cccaccataa cgtgctggta actaaggaca agggttgcgc    360
tcgttacggg acttaaccca acatctcacg acacgagctg acgacagcca tgcagcacct    420
gtctcagtgt tcccgaaggc accaaaccat ctctggtaag ttcactggat gtcaggcct     480 ggtaaggttc ttcgcgttgc ttcgaattaa accacatgct ccaccgcttg tgcgggcccc    540
cgtcaattca tttgagtttt aaccttgcgg ccgtactccc caggcggtca acttaatgcg    600
ttagctgcgc cactaaaatc tcaaggattc caacggctag ttgacatcgt ttacggcgtg    660
gactaccagg gtatctaatc ctgtttgctc ccacgctttc gcacctcag tgtcagtatg    720 agcccaggtg gtcgccttcg ccactggtgt tccttcctat atctacgcat ttcaccgcta    780
cacaggaaat tccaccaccc tctgccctac tcta                                814

<210> SEQ ID NO 10
<211> LENGTH: 1403
<212> TYPE: DNA
<213> ORGANISM: Pseudomonas sp.

<400> SEQUENCE: 10
gtaccgtcct cccgaaggtt agactagcta cttctggtgc aacccactcc catggtgtga      60
cgggcggtgt gtacaaggcc cggaacgta ttcaccgcga cattctgatt cgcgattact     120
```

```
agcgattccg acttcacgca gtcgagttgc agactgcgat ccggactacg atcggttttg    180
tgggattagc tccacctcgc ggcttggcaa ccctctgtac cgaccattgt agcacgtgtg    240
tagcccaggc cgtaagggcc atgatgactt gacgtcatcc ccaccttcct ccggtttgtc    300
accggcagtc tccttagagt gcccaccata acgtgctggt aactaaggac aagggttgcg    360
ctcgttacgg gacttaaccc aacatctcac gacacgagct gacgacagcc atgcagcacc    420
tgtctcaatg ctcccgaagg caccgatcca tctctggaaa gttcattgga tgtcaaggcc    480
tggtaaggtt cttcgcgttg cttcgaatta aaccacatgc tccaccgctt gtgcgggccc    540
ccgtcaattc atttgagttt taaccttgcg gccgtactcc ccaggcggtc aacttaatgc    600
gttagctgcg ccactaaaat ctcaaggatt ccaacggcta gttgacatcg tttacggcgt    660
ggactaccag ggtatctaat cctgtttgct ccccacgctt tcgcacctca gtgtcagtat    720
gagcccaggt ggtcgccttc gccactggtg ttccttccta tatctacgca tttcaccgct    780
acacaggaaa ttccaccacc ctctgcccta ctctagcttg ccagttttgg atgcagttcc    840
caggttgagc ccggggattt cacatccaac ttaacaaacc acctacgcgc gctttacgcc    900
cagtaattcc gattaacgct tgcaccctct gtattaccgc ggctgctggc acagagttag    960
ccggtgctta ttctgtcggt aacgtcaaaa cactaacgta ttaggttaat gcccttcctc   1020
ccaacttaaa gtgctttaca atccgaagac cttcttcaca cacgcggcat ggctggatca   1080
ggctttcgcc cattgtccaa tattcccac tgctgcctcc gtaggagtc tggaccgtgt    1140 ctcagttcca gtgtgactga tcatcctctc agaccagtta cggatcgtcg ccttggtgag   1200
ccattacctc accaactagc taatccgacc taggctcatc tgatagcgtg aggtccgaag   1260
atcccccact ttctcccgta ggacgtatgc ggtattagcg tcccttttcga cgttgtcc    1320 cccactacca ggcagattcc taggcattac tcacccgtcc ccgctgaat cagggagcaa    1380 gctccctcat ccgctcgact gca                                           1403
```

<210> SEQ ID NO 11
<211> LENGTH: 1397
<212> TYPE: DNA
<213> ORGANISM: Microbacterium oxydans

<400> SEQUENCE: 11

```
agtcgaacga gtgaacacgg agcttgctct gtgaggatca gtggcgaacg ggtgagtaac     60
acgtgagcaa cctgccctg actctgggat aagcgctgga acggcgtct aatactggat    120 atgtgacgtg accgcatggt ctgcgtctgg aaagaatttc ggttggggat gggctcgcgg    180
cctatcagct tgttggtgag gtaatggctc accaaggcgt cgacgggtag ccggcctgag    240
agggtgaccg gccacactgg gactgagaca cggcccagac tcctacggga ggcagcagtg    300
gggaatattg cacaatgggc gcaagcctga tgcagcaacg ccgcgtgagg gacgacggcc    360
ttcgggttgt aaacctcttt tagcagggaa gaagcgaaag tgacggtacc tgcagaaaaa    420
gcgccggcta actacgtgcc agcagccgcg gtaatacgta gggcgcaagc gttatccgga    480
attattgggc gtaaagagct cgtaggcggt ttgtcgcgtc tgctgtgaaa tccggaggct    540
caacctccgg cctgcagtgg gtacgggcag actagagtgc ggtagggag attggaattc    600 ctggtgtagc ggtggaatgc gcagatatca ggaggaacac cgatggcgaa ggcagatctc    660
tgggccgtaa ctgacgctga ggagcgaaag gtgggagca acaggcttag ataccctggt    720
agtccacccc gtaacgttgg gaactagttg tggggtccat tccacggatt ccgtgacgca    780
gctaacgcat taagttcccc gcctggggag tacggccgca aggctaaaac tcaaaggaat    840
```

-continued

```
tgacggggac cgcacaagc ggcggagcat gcggattaat tcgatgcaac gcgaagaacc    900
ttaccaaggc ttgacatata cgagaacggg ccagaaatgg tcaactcttt ggacactcgt    960
aaacaggtgg tgcatggttg tcgtcagctc gtgtcgtgag atgttgggtt aagtcccgca   1020
acgagcgcaa ccctcgttct atgttgccag cacgtaatgg tgggaactca tgggatactg   1080
ccggggtcaa ctcggaggaa ggtggggatg acgtcaaatc atcatgcccc ttatgtcttg   1140
ggcttcacgc atgctacaat ggccggtaca aagggctgca ataccgcgag gtggagcgaa   1200
tcccaaaaag ccggtcccag ttcggattga ggtctgcaac tcgacctcat gaagtcggag   1260
tcgctagtaa tcgcagatca gcaacgctgc ggtgaatacg ttcccgggtc ttgtacacac   1320
cgcccgtcaa gtcatgaaag tcggtaacac ctgaagccgg tggcctaacc ttttggagg    1380 gagccgtcga aggtggg                                                  1397
```

```
<210> SEQ ID NO 12
<211> LENGTH: 310
<212> TYPE: DNA
<213> ORGANISM: Enterobacter sp.

<400> SEQUENCE: 12
```

```
gccagcggtt aggccgggaa ctcaaaggag actgccagtg ataaactgga ggaaggtggg     60
gatgacgtca gtcatcatg gcccttacga ccagggctac acacgtgcta caatggcgca    120
tacaaagaga agcgatctcg cgagagccag cggacctcat aaagtgcgtc gtagtccgga   180
ttggagtctg caactcgact ccatgaagtc ggaatcgcta gtaatcgtga atcagaatgt   240
cacggtgaat acgttcccgg gccttgtaca caccgcccgt cacaccatgg gagtgggttg   300
caaaagaagt                                                          310
```

```
<210> SEQ ID NO 13
<211> LENGTH: 311
<212> TYPE: DNA
<213> ORGANISM: Pseudomonas sp.

<400> SEQUENCE: 13
```

```
tgccagcggg taatgccggg aactcaaagg agactgccgg tgataaaccg gaggaaggtg     60
gggatgacgt caagtcatca tggcccttac ggccagggct acacacgtgc tacaatggcg    120
catacaaaga gaagcgacct cgcgagagca agcggacctc ataaagtgcg tcgtagtccg    180
gatcggagtc tgcaactcga ctccgtgaag tcggaatcgc tagtaatcgt agatcagaat    240
gctacggtga atacgttccc gggccttgta cacaccgccc gtcacaccat gggagtgggt    300
tgcaaaagaa g                                                         311
```

```
<210> SEQ ID NO 14
<211> LENGTH: 383
<212> TYPE: DNA
<213> ORGANISM: Pantoea sp.

<400> SEQUENCE: 14
```

```
ctcgtgttgt gaaatgttgg gttaagtccc gcaacgagcg caacccttat cctttgttgc     60
cagcgattcg gtcgggaact caaaggagac tgccggtgat aaaccggagg aaggtgggga    120
tgacgtcaag tcatcatggc ccttacgagt agggctacac acgtgctaca atggcgcata    180
caaagagaag cgacctcgcg agagcaagcg gacctcacaa gtgcgtcgt agtccggatc     240 ggagtctgca actcgactcc gtgaagtcgg aatcgctagt aatcgtggat cagaatgcca    300
```
cggtgaatac gttcccgggc cttgtacaca ccgcccgtca caccatggga gtgggttgca    360
aaagaagtag gtagcttaac ctt    383

<210> SEQ ID NO 15
<211> LENGTH: 1247
<212> TYPE: DNA
<213> ORGANISM: Pseudomonas sp.

<400> SEQUENCE: 15
ccttgcgcta tcagatgagc ctaggtcgga ttagctagtt ggtgaggtaa tggctcacca    60
aggcgacgat ccgtaactgg tctgagagga tgatcagtca cactggaact gagacacggt    120
ccagactcct acgggaggca gcagtgggga atattggaca atgggcgaaa gcctgatcca    180
gccatgccgc gtgtgtgaag aaggtcttcg gattgtaaag cactttaagg tgggaggaag    240
ggttgtagat taatactctg caattttgac gttaccgcca gaatagcacc ggctaactct    300
gtgccagcag ccgcggtaat acagagggtg caagcgttaa tcggaattac tgggcgtaaa    360
gcgcgcgtag gtggtttgtt aagtcggatg tgaaatcccc gggctcaacc tgggaactgc    420
atccgaaact ggcaagctag agtatggtag agggtagtgg aatttcctgt gtagcggtga    480
aatgcgtaga tataggaagg aacaccagtg gcgaaggcga ctacctggac tgatactgac    540
actgaggtgc gaaagcgtgg ggagcaaaca ggattagata ccctggtagt ccacgccgta    600
aacgatgtca actagccgtt gggagccttg agctcttagt ggcgcagcta acgcattaag    660
ttgaccgcct ggggagtacg gccgcaaggt taaaactcaa atgaattgac ggggccccgc    720
acaagcggtg gagcatgtgg tttaattcga agcaacgcga gaaccttac caggccttga    780 catccaatga actttccaga gatggattgg tgccttcggg aacattgaga caggtgctgc    840
atggctgtcg tcagctcgtg tcgtgagatg ttgggttaag tcccgtaacg agcgcaaccc    900
ttgtccttag ttaccagcac gttatggtgg gcactctaag gagactgccg gtgacaaacc    960
ggaggaaggt ggggatgacg tcaagtcatc atggccctta cggcctgggc tacacacgtg    1020
ctacaatggt cggtacagag ggttgccaag ccgcgaggtg gagctaatct cacaaaaccg    1080
atcgtagtcc ggatcgcagt ctgcaactcg actgcgtgaa gtcggaatcg ctagtaatcg    1140
cgaatcagaa tgtcgcggtg aatacgttcc cgggccttgt acacaccgcc cgtcacacca    1200
tgggagtggg ttgcaccaga agtagctagt ctaaccttcg ggaggac    1247

<210> SEQ ID NO 16
<211> LENGTH: 670
<212> TYPE: DNA
<213> ORGANISM: Pseudomonas sp.

<400> SEQUENCE: 16
agctccacct cgcggcttgg caaccctctg taccgaccat tgtagcacgt gtgtagccca    60
ggccgtaagg gccatgatga cttgacgtca tccccacctt cctccggttt gtcaccggca    120
gtctccttag agtgcccacc ataacgtgct ggtaactaag gacaagggtt gcgctcgtta    180
cgggacttaa cccaacatct cacgacacga gctgacgaca gccatgcagc acctgtctca    240
atgttcccga aggcaccaat ccatctctgg aaagttcatt ggatgtcaag gcctggtaag    300
gttcttcgcg ttgcttcgaa ttaaaccaca tgctccaccg cttgtgcggg ccccgtcaa    360 ttcatttgag tttaaccctt gcggccgtac tccccaggcg gtcaacttaa tgcgttagct    420
gcgccactaa gagctcaagg ctcccaacgg ctagttgaca tcgtttacgg cgtggactac    480
cagggtatct aatcctgttt gctccccacg ctttcgcacc tcagtgtcag tatcagtcca    540

```
ggtagtcgcc ttcgccactg gtgttccttc ctatatctac gcatttcacc gctacacagg    600
aaattccact accctctacc atactctagc ttgccagttt cggatgcagt tcccaggttg    660
agcccgggga                                                           670
```

COMPOSITIONS AND METHODS COMPRISING ENDOPHYTIC BACTERIUM FOR APPLICATION TO GRASSES TO INCREASE PLANT GROWTH, SUPPRESS SOIL BORNE FUNGAL DISEASES, AND REDUCE VIGOR OF WEEDY COMPETITORS

CROSS REFERENCE TO RELATED APPLICATIONS

This application claims priority to PCT/US2016/43408 filed Jul. 21, 2016, the entire contents being incorporated herein by reference as though set forth in full.

SEQUENCE LISTING

The instant application contains a Sequence Listing with 16 sequences which has been submitted via EFS-Web and is hereby incorporated by reference in its entirety. Said ASCII copy, created on Jul. 20, 2017 is named SEQLIST and is 15 kb in size.

FIELD OF THE INVENTION

This invention relates to the fields of plant biology and endophytic bacteria. More specifically, the invention provides new strains of endophytic bacteria which provide beneficial features to the plant upon colonization of the same.

BACKGROUND OF THE INVENTION

Several publications and patent documents are cited throughout the specification in order to describe the state of the art to which this invention pertains. Each of these citations is incorporated by reference herein as though set forth in full.

Invasive *Phragmites australis* subsp. *australis* (Cav.) Trin., native to Eurasian wetlands, is an introduced grass in North America that displaces entire communities of native flora and fauna. This plant is highly competitive and generally out-competes other plants to produce large monospecific stands. It is increasingly becoming clear that microbes that form symbiotic associations with *Phragmites* play roles in increasing its invasive character (Clay et al., 2016). Soares et al. (2016a) recently demonstrated that endophytic bacteria isolated from tiller meristems were capable of increasing nitrogen assimilation into plants in greenhouse experiments. In another study, Soares et al. (2016b) showed that fungal endophytes that enter into roots of *Phragmites* growing in saline soils may enhance salt tolerance in the host, enabling it to thrive in high saline soils. Ernst, Mendgen and Wirsel (2003) demonstrated that a seed-borne fungal endophyte in genus *Stagonospora* enhanced biomass accumulation in experiments in microcosms. It is thus evident that symbiotic microbes may impact the aggressiveness of *Phragmites*.

SUMMARY OF THE INVENTION

In accordance with the present invention, a method of increasing root and shoot growth of a grass plant host, comprising inoculating the host grass or seed with one or more biologically pure *Pseudomonas* spp., *Microbacterium* ssp. or *Enterobacter* ssp. endophyte strains isolated from *Phragmites australis*, which are heterologously disposed to said grass plant host, and effective to increase one or more of root growth promotion, shoot growth promotion, resistance to salt stress, competition with undesirable plant species and resistance to fungus in a plant produced from the seed, when compared to a reference plant grown under the same conditions. In certain embodiments, the bacteria comprise specific rDNA sequences selected from the group consisting of SEQ ID NO: 1-16 or sequences having at least 90%, at least 95%, or at least 98% identity therewith. In a particularly preferred embodiment, the endophytic bacteria comprise one or more of Sandy LB4, Sandy LB6, Sandy Y8, RoY12, RoLB13w, WY9y, WY6, West 9, WY14, RiY3, SandyY7w, RiLB4, SY1, SY5, WY9w, and *Microbacterium oxydans* B2. The aforementioned method can also be used to advantage to suppress growth of soil borne fungal pathogens of said host grass relative to host grasses which have not been inoculated with the one or more endophyte. Plants treated with the method may also exhibit increased resistance to disease relative to untreated host plants. Inoculated plants also are effective to reduce competitiveness of distantly related competitor weeds of said grass plant host.

The host grass includes, without limitation, a turf and forage grass selected from *Agrostis* spp., *Poa* spp., *Festuca* spp., *Lolium* spp., *Cynodon* spp., *Zoysia* spp., *Koleria* spp., *Paspalum* spp., *Panicum* spp., *Stenotaphrum* spp., *Eremochloa* spp. and *Danthonia* spp., *Triticum aestivum*, *Oryza sativa*, *Avena sativa*, *Hordeum vulgare*, *Panicum miliaceum*, *Eleusine coracana*, *Sorghum bicolor*, *Pennisetum glaucum*, *Setaria italica*, *Zea maydis*. *Agrostis* spp., *Poa* spp., *Festuca* spp., *Lolium* spp., *Cynodon* spp., *Zoysia* spp., *Koleria* spp., and *Danthonia* spp. In a preferred embodiment of the method, the host grass is a food grass crop selected from *Oryza sativa*, *Triticum aestivum*, and *Zea maydis*. In yet another preferred embodiment, the host grass is a Pooideae grass. In certain aspects of the invention, the bacteria are present in a synthetic seed ball. Plants may also be sprayed with a liquid formulation comprising the bacteria. In another embodiment, the bacteria are present in a controlled release fertilizer formulation.

The invention also encompasses a synthetic combination comprising at least one purified bacterial population in association with a seed of a turf and forage grass, wherein the purified bacterial population comprises a seed bacterial endophyte that is heterologously disposed to the turf or forage grass seed and is selected from one or more of Sandy LB4, Sandy LB6, Sandy Y8, RoY12, RoLB13w, WY9y, WY6, West 9, WY14, RiY3, SandyY7w, WY9w, RiLB4, SY1, SY5 and *Microbacterium oxydans* B2, the seed bacterial endophyte being present in the synthetic combination at a concentration of at least $10^3$ CFU/seed on the surface of a seed, and in an amount effective to increase one or more of root growth promotion, shoot growth promotion, resistance to salt stress, competition with undesirable plant species and increase resistance to fungus in a plant produced from the seed, when compared to an untreated reference plant grown under the same conditions. In this embodiment of the invention, the bacteria may be lyophilized, encapsulated in an alginate bead formulation, or present in a seed ball. Grass seed to be treated, include without limitation, seeds from a grass selected from *Agrostis* spp., *Poa* spp., *Festuca* spp., *Lolium* spp., *Cynodon* spp., *Zoysia* spp., *Koleria* spp., and *Danthonia* spp. In a one embodiment, the is *Microbacterium oxydans* B2 and said seed is a rice seed.

In another aspect of the invention, a method of reducing undesirable weed growth in soils comprising turf and forage grasses, comprising drenching or treating the soil with one or more biologically pure *Pseudomonas* spp. endophyte strains wherein said strains reduce weed growth relative to weed growth observed in untreated soil is provided. In one embodiment, the one or more *Pseudomonas* spp. is Sandy LB4 and/or West 9.

In certain aspects, the synthetic combination comprises a combination of bacteria selected from the group consisting of i) protease positive strains consisting of Sandy LB4 or Sandy LB6 in combination with strains SY1 or SY5; ii) protease positive strains WY6 or WY14 in combination with protease negative strain WY9y and iii) phosphatase negative strain *Microbacterium oxydans* B2 in combination with phosphatasepositive strains Sandy LB4 or Sandy LB6 which can act synergistically to increase root and shoot growth of grass plant hosts. An exemplary method comprises artificially inoculating the host grass with one or more biologically pure *Pseudomonas* spp. endophyte strains wherein said strains confer protection to the host grass. Preferably, said one or more *Pseudomonas* sp. is Sandy LB4 and West 9 used alone or in combination.

BRIEF DESCRIPTION OF THE DRAWINGS

FIG. 2A. *Cynodon dactylon* (Bermuda grass) Seedlings growing on 0.7% agarose and stained with DAB for reactive oxygen. FIG. 2B. Bermuda grass (*Cynodon dactylon*) grass seedling root in agarose without bacteria showing absence of root hairs.

FIG. 3A. Bacterial strain West 9 colonizes the Bermuda grass seedling root-tip meristem and becomes intracellular in meristem cells then transmits to all parts of the seedling root and root hairs as the meristem cells divide. In these seedlings root hairs form very close to the root tip. West 9 restores root hair development in sterile seedlings. Root stained in agarose using DAB (diaminobenzidine) to visualize reactive oxygen ($H_2O_2$) production around bacteria. FIG. 3B. Root hairs (arrow) behind the root-tip are seen to stain brown internally due to production of reactive oxygen in the vicinity of the intracellular bacteria.

FIG. 4A. Early developing root hairs show internal presence of the spherical wall-less L-forms (arrows) of bacterial strain West 9. Roots were stained with DAB then counterstained with aniline blue stain. FIG. 4B. Early developing root parenchyma cells also show chains of the spherical L-form bacteria. The root was stained with DAB then counterstained with aniline blue stain. FIG. 4C. Cells from the root meristem show internal presence of bacteria (arrows). FIG. 4D. The bacteria are degraded internally. They are seen to swell and become clear internally (arrows). Clusters of degraded bacteria are seen in these root parenchyma cells. FIG. 4E. More degrading bacteria (arrows) in root parenchyma cells. Bacterial L-forms swell as their internal contents vanish due to degradation.

FIG. 5A. As the root continues to develop the bacteria within root hairs and root parenchyma cells are seen to disappear, apparently due to complete degradation by the root cells. Here several root hairs are seen to be free of internal bacteria (arrows). Bacteria that were intercellular are not degraded and remain as endophytes in the plant. FIG. 5B. In older parts of the root all root hairs are seen to be free of internal bacteria and reactive oxygen staining (brown coloration). In the parenchyma cells of the root axis, the brown coloration also lessens due to degradation of the internal bacteria.

FIG. 6A. *Poa annua* seedling root in agarose without bacteria showing absence of root hairs. Stained using DAB to visualize reactive oxygen. FIG. 6B. *Poa annua* seedling root bearing strain West 9, showing production of root hairs. FIG. 6C. *Poa annua* root hair showing internal bacteria (arrows).

FIG. 7A. Strain Sandy LB4 (also from *Phragmites*) is also a meristem colonizer. It is shown here in a Bermuda grass seedling root. FIG. 7B. The bacteria appear to persist longer in Bermuda grass seedling roots than strain West 9. It appears that the effect of Sandy LB4 in Bermuda grass seedlings is of longer duration than that of West 9.

FIG. 8A. *Rumex crispus* (Curly dock). FIG. 8B. Strain Sandy LB4 from *Phragmites* in root hair of *Rumex crispus*. Root hair blockage may affect the absorptive function of root hairs. This may reduce the competitive ability of seedlings. FIG. 8C. Normal root hair function involves internal cytoplasmic streaming. Cytoplasmic streaming cessation in blocked hairs may reduce nutrient absorption.

FIG. 9A. Dandelion seedlings (3-wk-old) showing high mortality when colonized by *Phragmites* bacterium Sandy LB4. FIG. 9B. Dandelion seedlings from inhibition experiment in soil.

DETAILED DESCRIPTION OF THE INVENTION

Figure 1A:
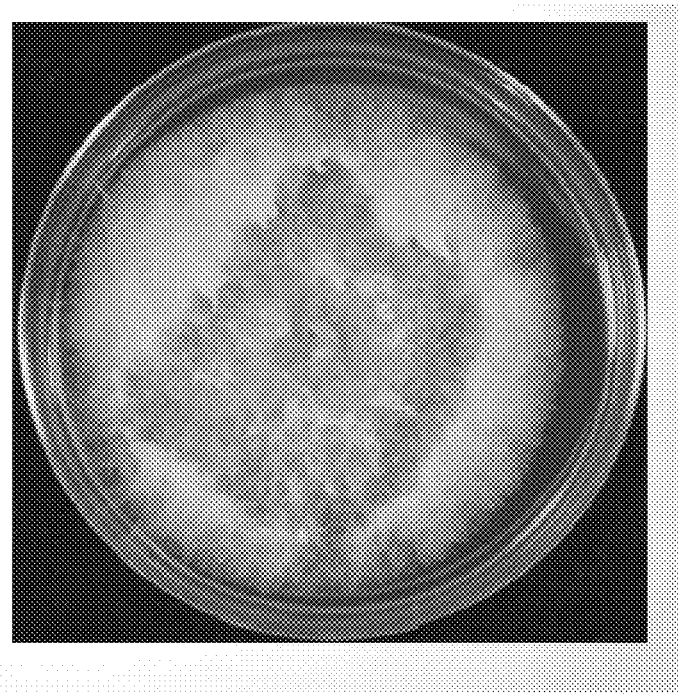
FIGS. 1A-1D. Fungus without bacteria (FIG. 1A) *Pseudomonas fluorescens* Sandy LB4, (FIG. 1B) *Pseudomonas* sp. West 9 (FIG. 1C) and *Microbacterium oxydans* B2 (FIG. 1D) were co-cultured on LBA with soil fungi *Sclerotinia homeocarpa*, (the causal agent of Dollar spot disease inturfgrass) for 7 days. Formation of zones of inhibition are shown.
Figure 1B:
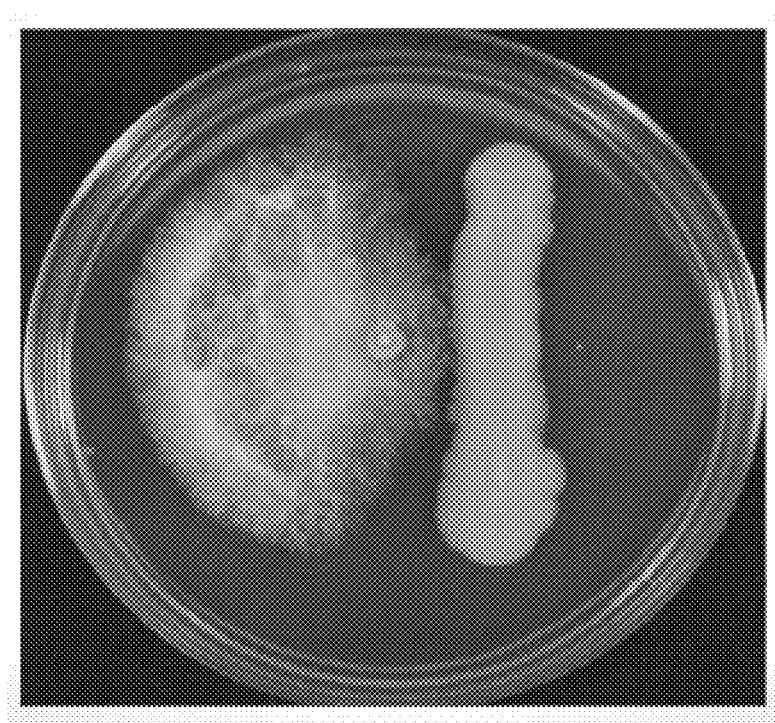
Figure 1C:
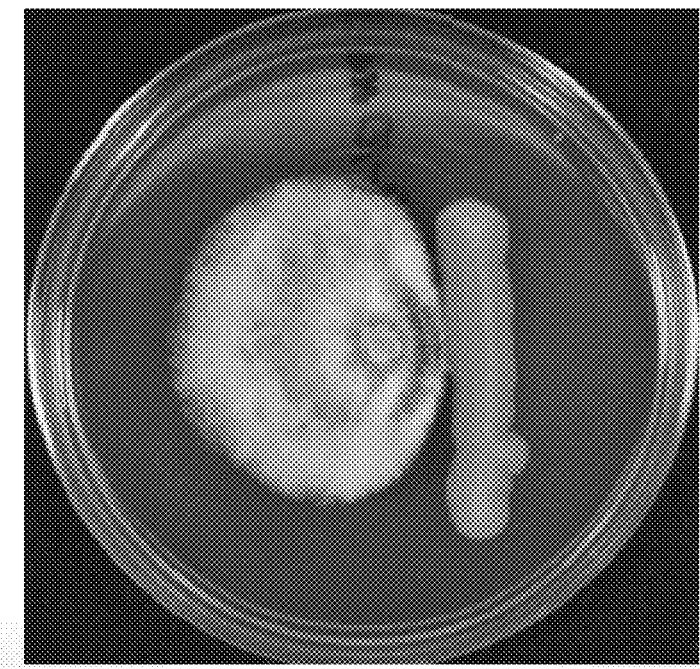
Figure 1D:
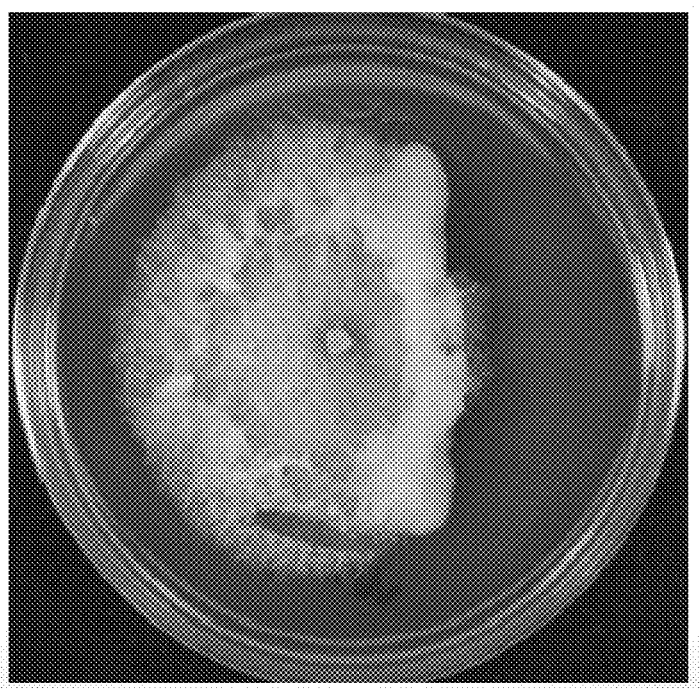

*Phragmites australis* is an invasive grass that decreases biodiversity and produces dense stands in North America. In the present invention, we tested the hypothesis that invasive *Phragmites australis* establishes mutualisms with endophytic microbes that increase its growth, improve its ability to survive stressful environments and resist pathogens, and contribute to its competitive capacity against other plant species. Ten bacterial strains were isolated from the surfaces of *Phragmites* seeds collected from natural stands at four sites in New Jersey. 80% of the isolates were identified to genus *Pseudomonas*. Using a surrogate test grass *Cynodon dactylon* in seedling assays we determined that two of the isolated strains Sandy LB4 (*Pseudomonas fluorescens*; deposited as accession number NRRL-B67308) and West 9 (*Pseudomonas* sp.; deposited as accession number NRRL-B67307) were endophytes that enter into plant meristems and become intracellular within cells of root tissues. These bacterial strains, along with an endophyte (*Microbacterium oxydans* B2; deposited as accession number NRRL-B67470) isolated from *Phragmites* shoot tissues, were found to increase plant growth using the surrogate grass host *Poa annua*. These strains were also found to slightly improve seed germination and increase seedling root branching in assays using *Poa annua*. Strains Sandy LB4 and West 9 were further shown to protect plants from damping off disease caused by fungal pathogen *Fusarium oxysporum* using *Poa annua* as the surrogate host plant in magenta box experiments. To evaluate whether *Phragmites* bacteria might play a role in inhibiting growth of competitor plant species we conducted experiments using dandelion (*Taraxacum officionale*) and curly dock (*Rumex crispus*). In these experiments we found that one of the endophytic strains, Sandy LB4, has the capacity to increase mortality in seedlings of both competitor species. Further, Sandy LB4 reduces the growth rates of both competitor plant species and increases their susceptibility to diseases.

I. Definitions

An "endophyte" or "endophytic microbe" is an organism that lives within a plant or is otherwise associated therewith. Endophytes can occupy the intracellular or intercellular spaces of plant tissue, including the leaves, stems, flowers, fruits, seeds, or roots. An endophyte can be either a bacterial or a fungal organism that can confer a beneficial property to a plant such as an increase in yield, biomass, resistance, or fitness in its host plant. As used herein, the term "microbe" is sometimes used to describe an endophyte.

Several strains of the bacteria described herein can be identified by their distinct ribosomal 16S sequences. 16S ribosomal RNA (or 16S rRNA) is the component of the 30S small subunit of a prokaryotic ribosome that binds to the Shine-Dalgarno sequence. The genes coding for it are referred to as 16S rRNA gene and are used in reconstructing phylogenies, due to the slow rates of evolution of this region of the gene. Ribosomal RNA sequences from the bacteria described herein are provided in SEQ ID NOS: 1-16

As used herein, "sequence identity" generally refers to the percent identity of nucleotide bases or amino acids comparing a first polynucleotide or polypeptide to a second polynucleotide or polypeptide using algorithms having various weighting parameters. Sequence identity between two polynucleotides or two polypeptides can be determined using sequence alignment by various methods and computer programs (e.g., BLAST, CS-BLAST, FASTA, HMMER, L-ALIGN, and the like) available through the worldwide web at sites including but not limited to GENBANK (on the world wide web at ncbi.nlm.nih.gov/genbank/) and EMBL-EBI (on the world wide web at ebi.ac.uk.). Sequence identity between two polynucleotides or two polypeptide sequences is generally calculated using the standard default parameters of the various methods or computer programs. A high degree of sequence identity, as used herein, between two polynucleotides or two polypeptides is typically between about 90% identity and 100% identity, for example, about 90% identity or higher, preferably about 95% identity or higher, more preferably about 98% identity or higher. A moderate degree of sequence identity, as used herein, between two polynucleotides or two polypeptides is typically between about 80% identity to about 85% identity, for example, about 80% identity or higher, preferably about 85% identity. A low degree of sequence identity, as used herein, between two polynucleotides or two polypeptides is typically between about 50% identity and 75% identity, for example, about 50% identity, preferably about 60% identity, more preferably about 75% identity.

The terms "promoting plant growth" and "stimulating plant growth" are used interchangeably herein, and refer to the ability to enhance or increase at least one of the plant's height, weight, leaf size, root size, shoot length, stem size, competition with competitor plants, resistance to fungal infection, increased protein yield from the plant or increased grain yield of the plant. Particular formulations to be applied in spraying forms such as water dispersible concentrates or wettable powders may contain surfactant such as wetting and dispersing agents, e.g., the condensation product of formaldehyde with naphthalene sulphonate, an alkyl-arylsulphonate, a lignin sulphonate, a fatty alkyl sulphate an ethoxylated alkylphenol and an ethoxylated fatty alcohol.

As used herein the terms "spray" or "spraying" include the technique of applying to an exterior surface an ejected liquid material.

As used herein, the terms "coat" or "coating" include application, typically of a liquid or flowable solid, to an exterior surface such as a seed.

As used herein, a "stabilizer" includes a chemical compound that can be added to a formulation to prolong the stability and/or viability of components of the formulation, a critical aspect of product shelf-stability. A stabilizer can be one of a variety of compounds, such as a dessicant.

As used herein, a "preservative" includes any chemical compound and/or physical conditions that prevent the decomposition of organic constituents of seeds treated with formulations. Chemical preservatives could include, for example, synthetic or non-synthetic antioxidants and physical preservatives could include, for example, refrigeration, freeze-drying or drying.

According to an embodiment the at least one dispersing agent can be in the range of about 2% to about 60% on a dry weight by weight basis. Various dispersing agents are commercially available for use in agricultural compositions, such as those marketed by Rhone Poulenc, Witco, Westvaco, International Speciality products, Croda chemicals, Borregaard, BASF, Rhodia, etc. According to an embodiment the dispersing agents which can be used in the agricultural composition can be chosen from a group comprising polyvinylpyrrolidone, polyvinylalcohol, lignosulphonates, phenyl naphthalene sulphonates, ethoxylated alkyl phenols, ethoxylated fatty acids, alkoxylated linear alcohols, polyaromatic sulfonates, sodium alkyl aryl sulfonates, glyceryl esters, maleic anhydride copolymers, phosphate esters, condensation products of aryl sulphonic acids and formaldehyde, condensation products of alkylaryl sulphonic acids and formaldehyde, addition products of ethylene oxide and fatty acid esters, salts of addition products. of ethylene oxide and fatty acid esters, sulfonates of condensed naphthalene, addition products of ethylene oxide and fatty acid esters, salts of addition products of ethylene oxide and fatty acid esters, lignin derivatives, naphthalene formaldehyde condensates, sodium salt of isodecylsulfosuccinic acid half ester, polycarboxylates, sodium alkylbenzenesulfonates, sodium salts of sulfonated naphthalene, ammonium salts of sulfonated naphthalene, salts of polyacrylic acids, salts of phenolsulfonic acids and salts of naphthalene sulfonic acids. However, those skilled in the art will appreciate that it is possible to utilize other dispersing agents known in the art without departing from the scope of the claims of the present invention.

In some embodiments, a bacterial endophyte is a seed-origin bacterial endophyte. As used herein, a "seed-origin bacterial endophyte" refers to a population of bacteria associated with or derived from the seed of a grass plant. For example, a seed-origin bacterial endophyte can be found in mature, dry, undamaged (e.g., no cracks, visible fungal infection, or prematurely germinated) seeds. The bacteria can be associated with or derived from the surface of the seed; alternatively, or in addition, it can be associated with or derived from the interior seed compartment (e.g., of a surface-sterilized seed). In some cases, a seed-origin bacterial endophyte is capable of replicating within the plant tissue, for example, the interior of the seed. Also, in some cases, the seed-origin bacterial endophyte is capable of surviving desiccation.

Seed-origin means that the bacterial entity is obtained directly or indirectly from the seed surface or seed interior compartment or is obtainable from a seed surface or seed interior compartment. For example, a seed-origin bacterial entity can be obtained directly or indirectly from a seed surface or seed interior compartment when it is isolated, or isolated and purified, from a seed preparation; in some cases, the seed-origin bacterial entity which has been isolated, or isolated and purified, may be cultured under appropriate conditions to produce a purified bacterial population consisting essentially of a seed-origin bacterial endophyte. A seed-origin bacterial endophyte can be considered to be obtainable from a seed surface or seed interior compartment if the bacteria can be detected on or in, or isolated from, a seed surface or seed interior compartment of a plant.

In some embodiments, the present invention contemplates methods of manually or mechanically combining an endophyte described herein with one or more plant elements, such as a seed, a leaf, or a root, in order to confer an improved agronomic trait or improved agronomic trait potential to said plant element or host plant. In some embodiments, the present invention contemplates methods of manually or mechanically combining a plurality of endophytes described herein with one or more plant elements.

As used herein, an endophyte is "heterologously disposed" when mechanically or manually applied, artificially inoculated or disposed onto or into a plant element, seedling, plant or onto or into a plant growth medium or onto or into a treatment formulation so that the endophyte exists on or in said plant element, seedling, plant, plant growth medium, or treatment formulation in a manner not found in nature prior to the application of the endophyte, e.g., said combination which is not found in nature. In some embodiments, such a manner is contemplated to include: the presence of the endophyte; presence of the endophyte in a different number, concentration, or amount; the presence of the endophyte in or on a different plant element, tissue, cell type, or other physical location in or on the plant; the presence of the endophyte at different time period, e.g. developmental phase of the plant or plant element, time of day, time of season, and combinations thereof. In some embodiments, plant growth medium is soil, a hydroponic apparatus, or artificial growth medium such as commercial potting mix. In some embodiments, the plant growth medium is soil in an agricultural field. In some embodiments, the plant growth medium is commercial potting mix. In some embodiments, the plant growth medium is an artificial growth medium such as germination paper. As a non-limiting example, if the plant element or seedling or plant has an endophyte normally found in the root tissue but not in the leaf tissue, and the endophyte is applied to the leaf, the endophyte would be considered to be heterologously disposed. As a non-limiting example, if the endophyte is naturally found in the mesophyll layer of leaf tissue but is applied to the epithelial layer, the endophyte would be considered to be heterologously disposed. As a non-limiting example, an endophyte is heterologously disposed at a concentration that is at least 1.5 times, between 1.5 and 2 times, 2 times, between 2 and 3 times, 3 times, between 3 and 5 times, 5 times, between 5 and 7 times, 7 times, between 7 and 10 times, 10 times greater, or even greater than 10 times higher number, amount, or concentration than that which is naturally present. As a non-limiting example, an endophyte is heterologously disposed on a seedling if that endophyte is normally found at the flowering stage of a plant and not at a seedling stage.

The compositions provided herein are preferably stable. The seed-origin bacterial endophyte is optionally shelf stable, where at least 10% of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf stable formulation is in a dry formulation, a powder formulation, or a lyophilized formulation. In some embodiments, the formulation is formulated to provide stability for the population of bacterial endophytes. In one embodiment, the formulation is substantially stable at temperatures between about 0° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

An agricultural plant can be a monocotyledonous (i.e., an "agricultural grass plant") or a dicotyledonous plant typically used in agriculture. An agricultural grass plant includes, but is not limited to, maize (*Zea mays*), common wheat (*Triticum aestivum*), spelt (*Triticum spelta*), einkorn wheat (*Triticum monococcum*), emmer wheat (*Triticum dicoccum*), durum wheat (*Triticum durum*), Asian rice (*Oryza sativa*), African rice (*Oryza glabaerreima*), wild rice (*Zizania aquatica, Zizania latifolia, Zizania palustris, Zizania texana*), barley (*Hordeum vulgare*), Sorghum (*Sorghum bicolor*), Finger millet (*Eleusine coracana*), Proso millet (*Panicum miliaceum*), Pearl millet (*Pennisetum glaucum*), Foxtail millet (*Setaria italic*), Oat (*Avena sativa*), Triticale (*Triticosecale*), rye (*Secale cereal*), Russian wild rye (*Psathyrostachys juncea*), bamboo (*Bambuseae*), grasses, including *Agrostis* spp., *Poa* spp., *Festuca* spp., *Lolium* spp., *Cynodon* spp., *Zoysia* spp., *Koleria* spp., *Danthonia* spp., or sugarcane (e.g., *Saccharum arundinaceum, Saccharum barberi, Saccharum bengalense, Saccharum edule, Saccharum munja, Saccharum officinarum, Saccharum procerum, Saccharum ravennae, Saccharum robustum, Saccharum sinense*, or *Saccharum spontaneum*).

A "host plant" includes any plant, particularly an agricultural plant, which an endophytic microbe such as a seed-origin bacterial endophyte can colonize. As used herein, a microbe is said to "colonize" a plant or seed when it can be stably detected within the plant or seed over a period time, such as one or more days, weeks, months or years; in other words, a colonizing microbe is not transiently associated with the plant or seed. A preferred host plant is a cereal plant.

As used herein, a "reference agricultural plant" is an agricultural plant of the same species, strain, or cultivar to which a treatment, formulation, composition or endophyte preparation as described herein is not administered/contacted. Exemplary reference agricultural plants are described herein. A reference agricultural plant, therefore, is identical to the treated plant with the exception of the presence of the endophyte and can serve as a control for detecting the effects of the endophyte that is conferred to the plant.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

A "bacterial network" means a plurality of endophyte entities (e.g., bacteria, fungi, or combinations thereof) co-localized in an environment, such as on or within a grass agricultural plant. Preferably, a bacterial network includes two or more types of endophyte entities that synergistically interact, such synergistic endophytic populations capable of providing a benefit to the agricultural seed, seedling, or plant derived thereby.

An "increased yield" can refer to any increase in biomass or seed or fruit weight, seed size, seed number per plant, seed number per unit area, bushels per acre, tons per acre, kilo per hectare, or carbohydrate yield. Typically, the particular characteristic is designated when referring to increased yield, e.g., increased grain yield or increased seed size.

A "transgenic plant" includes a plant or progeny plant of any subsequent generation derived therefrom, wherein the DNA of the plant or progeny thereof contains an exogenous DNA not naturally present in a non-transgenic plant of the same strain. The transgenic plant may additionally contain sequences that are native to the plant being transformed, but wherein the "exogenous" gene has been altered in order to alter the level or pattern of expression of the gene, for example, by use of one or more heterologous regulatory or other elements.

The terms "pathogen" and "pathogenic" in reference to a bacterium includes any such organism that is capable of causing or affecting a disease, disorder or condition of a host containing the organism.

As used herein, an "agricultural seed" is a seed used to grow a plant typically used in agriculture (an "agricultural plant"). The seed may be of a monocot or dicot plant, and may be planted for the production of an agricultural product, for example grain, food, fiber, etc. As used herein, an agricultural seed is a seed that is prepared for planting, for example, in farms for growing.

In some cases, the present invention contemplates the use of microbes that are "compatible" with agricultural chemicals, for example, a fungicide, an anti-bacterial compound, or any other agent widely used in agricultural which has the effect of killing or otherwise interfering with optimal growth of microbes. As used herein, a microbe is "compatible" with an agricultural chemical when the microbe is modified, such as by genetic modification, e.g., contains a transgene that confers resistance to an herbicide, or is adapted to grow in, or otherwise survive, the concentration of the agricultural chemical used in agriculture. For example, a microbe disposed on the surface of a seed is compatible with the fungicide metalaxyl if it is able to survive the concentrations that are applied on the seed surface.

In some embodiments, an agriculturally compatible carrier can be used to formulate an agricultural formulation or other composition that includes a purified bacterial preparation. As used herein an "agriculturally compatible carrier" refers to any material, other than water, which can be added to a seed or a seedling without causing or having an adverse effect on the seed (e.g., reducing seed germination) or the plant that grows from the seed, or the like.

As used herein, a "portion" of a plant refers to any part of the plant, and can include distinct tissues and/or organs, and is used interchangeably with the term "tissue" throughout.

A "population" of plants, as used herein, can refer to a plurality of plants that were subjected to the same inoculation methods described herein, or a plurality of plants that are progeny of a plant or group of plants that were subjected to the inoculation methods. In addition, a population of plants can be a group of plants that are grown from coated seeds. The plants within a population will typically be of the same species, and will also typically share a common genetic derivation.

A "reference environment" refers to the environment, treatment or condition of the plant in which a measurement is made. For example, production of a compound in a plant associated with a purified bacterial population (e.g., a seed-origin bacterial endophyte) can be measured in a reference environment of drought stress, and compared with the levels of the compound in a reference agricultural plant under the same conditions of drought stress. Alternatively, the levels of a compound in plant associated with a purified bacterial population (e.g., a seed-origin bacterial endophyte) and reference agricultural plant can be measured under identical conditions of no stress.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

II. Methods of the Invention

The invention relates to a process and method for the production and use of endophytes as plant inoculants products that provide unique inoculant feature/benefits for the promotion of plant vigor, health, growth and yield comprising bacteria isolated from *Phragmites*, e.g., Strains Sandy LB4, SY1 and strain West 9. Several of these new strains of bacteria have been deposited with the NRRL Agriculture Research Service Culture Collection (herein after "NRRL") under the terms of the Budapest Treaty, under accession numbers provided herein.

The invention also relates to a process and method for producing economically acceptable quantities of preparations of the aforementioned bacteria. The invention further relates to an endophyte product(s) produced by such processes and methods. The endophyte product(s) may comprise a solid substrate of, for example, certain cereals e.g. rye, which contain sufficient natural emulsifiers in the form of various proteins, lignin, to provide the bacteria with excellent natural dispersing/wetting/sticker agents that allows for rapid site occupation on/in plants. The product formulation allows/enables practical use and application of the product(s) to roots, stems, leaves, flowers, bulbs, etc of plants as a water-based sprayable formulations or as a dusts for other uses e.g. seed treatment, or as dusts for insect/mite vectors. The product when applied to seeds, roots, stems, leaves, flowers, wounds or cut surfaces of plants enables the endophyte to act as an inoculant within the tissues of plants. The product provides improved roots, leaf, stem and or vegetative bud (flowers) growth to plants and or enhances/improves the germination and emergence of seeds and also causes mortality in neighboring competitor species. The product provides for reduction of environmental or cultural stress to plants e.g. root loss due to trimming, pruning, cutting or other stresses. The product provides improved crop quality and faster development to marketability of the crop. The product provides for a reduction in the dependency on chemical pesticides for pest control e.g. control of *Botrytis, Fusarium, Pythium* and the like. The product can be used for the production of a variety of greenhouse, horticultural and agronomic field crops. The composition of the invention can be a plant inoculant composition comprising the bacteria described above in admixture with an agrochemically acceptable diluent or carrier. The invention also relates to a method of enhancing growth, health vigor or yield of a plant which method comprises applying the plant inoculant composition of the invention to a plant or plant locus. The invention further relates to a method of combating a plant fungus which method comprises applying an antifungal effective amount of the composition.

Lyophilization Procedure

Freeze drying bacteria (lyophilization) is a very well established method for the archiving and long-term storage. Initial reports of freeze drying bacteria can be found in the middle of last century. The approaches used vary widely, but they all following the standard process associated with lyophilization, namely the freezing of the sample, application of a high vacuum, warming of the sample while under vacuum which causes water sublimation, driving off excess water through a drying phase, and finally sealing of the sample to prevent water uptake. This general process is used to preserve bacteria, fungi, yeasts, proteins, nucleic acids, and any other molecules which may be degraded due to the presence of water.

Thus in one aspect of the invention, one or more of the endophytic bacteria will be applied to a plant or a plant part (such as seeds) as a lyophilized (freeze-dried) powder. In brief, the liquid culture will be: centrifuged, re-suspended in a lyophilization medium which will optionally include cryoprotectants and biological- and/or chemical-oxygen scavengers, transferred to a shelf lyophilizer, lyophilized, and packaged for transport and storage.

In an alternative approach, one or more bacteria may be encapsulated in alginate beads enriched with humic acid as described by Young C C et al., Biotechnol Bioeng. 2006 Sep. 5; 95(1):76-83. Also see "Alginate beads as a storage, delivery and containment system for genetically modified PCB degrader and PCB biosensor derivatives of *Pseudomonas fluorescens* F113 B" by Power et al., Journal of Applied Microbiology 110, 1351-1358, 2011. Other approaches include coating seeds with preparations comprising the endophytic bacteria of the invention. For example, Sandy LB4 can be incorporated into a carrier, which include without limitation, alginate (micro-bead formation), chitosan, carboxymethylcellulose-starch, clay, finely-ground peat mixed with calcium carbonate, methacrylic acid, bio-char and biogels. In certain embodiments, carrier and Sandy LB4 may be mixed with additives (including: adhesives, nutrients, surfactants and stabilizers).

The carrier and Sandy LB4, for example, (with additives) can be applied to seeds of grass crops using a commercial seed dressing machine (e.g., MAYJOY High Speed Seeds Dressing Machine/Corn Seed Dresser).

Sandy LB4 may also be used as an additive to create seed balls. In this approach, clay mixed with freeze-dried preparation of Sandy LB4 and seeds (2-3) are added to the center of a small clay ball. The seed balls are then dried and stored for future use.

Sandy LB4 can also be applied to host plants in soil drenching approaches. For example, freeze dried preparation of Sandy LB4 can be mixed with a liquid carrier (comprising water, buffers, plant nutrients, and microbial nutrients). This liquid preparation of bacterium and carrier (with additives) may be applied to the soil around plant or seed or in the alternative be applied to soil and plants using a commercial sprayer.

The following materials and methods are provided to facilitate the practice of the present invention.

Seed Collection

Seeds of *P. australis* were collected at four sites in New Jersey, including Sandy Hook peninsula, and towns of South River, West Windsor and Robbinsville.

Seed Preparation

Seeds were cleaned of associated awns, lemmas and paleas by rubbing seeds between a fine mesh screen and wooden block. Seeds were washed with agitation in sterile water then the water was discarded. Seeds were then washed a second time in 1-mL of sterile water after which the water was spread over the surface of agar plates containing trypticase soy agar (TSA), Luria Bertani Agar (LBA) and Yeast Extract Sucrose Agar (YESA) and plates incubated at room temperature for a 24-48 hr period. Colonies were removed and streaked to obtain pure cultures. A total of 16 isolates were obtained from *P. australis* seeds using this method.

Bacterial Identification and Characterization

Genomic DNA from bacteria was isolated using QIAGEN miniprep kits. Bacterial identifications were made by use of 16S rDNA sequences after methods employed by Lane (1991) (Table1). For Sandy LB4 we used the recA gene to identify the bacterium to species. Sequences were compared to GenBank accessions using BLASTn (found on the world wide web at ncbi.nlm.nih.gov). Cultures on LB agar were also observed under ultraviolet light using an ultraviolet mineralogical lamp (UVGL-21, long wave UV-366 nm, UVP, San Gabriel, Calif., USA). Phosphate solubilization was assessed by culturing bacteria on Pikovskayas agar, while protease testing was done by culturing in skim milk agar.

Endophytism Determination

Two of the *Phragmites* seed bacteria (*Pseudomonas fluorescens* Sandy LB4 and *Pseudomonas* sp. West 9) were selected along with bacteria *Microbacterium oxydans* B2 (from *Phragmites* shoots) and *Bosea thiooxidans* TBN (from Japanese knotweed). These bacteria were screened to determine their capacity to become endophytic in grass roots. Bermuda grass (*Cynodon dactylon*) was used to evaluate endophytism because seeds could be surface sterilized and seedlings would readily grow in sterile agarose medium. Seeds without husks were surface disinfected by agitation in 4% NaOCl solution for 45 mins. Seeds were washed thoroughly by agitation in several washes of sterile water until chlorine odor could not be detected on seeds. Seeds were then placed onto 0.7% agarose in Petri dished. To inoculate seeds one drop of a water suspension of bacteria (at approximately 0.5 OD, 600 nm) was placed onto each seed. For each treatment each plate contained 10-15 seeds, with 5 replicates per treatment. An axenic control was also done to confirm behavior of seedlings without bacteria. Plates were incubated at room temperature for 7-10 days.

Visualization of Bacteria in/on Seedling Roots

To visualize bacteria in/on seedling roots, plates bearing seedlings were flooded and stained with a solution of 3, 3'-diaminobenzidine (DAB) using SIGMAFAST®3, 3'-diaminobenzidine tablets from Sigma (White et al., 2014) and incubated at laboratory ambient temperature overnight for staining. Plates were then washed of excess DAB and the seedling roots examined through the reverse of the Petri plate using a compound light microscope. Intracellular penetration of root cells was indicated by dark red or brown staining within root hairs and/or root parenchyma cells.

Assessment of Capacity for Plant Growth Promotion

To assess plant growth promotion, *Pseudomonas fluorescens* Sandy LB4, *Pseudomonas* sp. West 9, *Microbacterium oxydans* B2 and *Bosea thiooxidans* TBN were inoculated onto previously surface disinfected (40 mins agitation in 4% NaOCl) seeds of *Poa annua* by soaking seeds in a suspension of bacteria (at approximately 0.5 OD, 600 nm). Controls were not inoculated with bacteria. Seeds were planted in sterile soil in magenta boxes with approximately 15 plants/treatment and placed under florescent lights in the laboratory for 37 days. Plants were harvested by removal from soil and roots wiped of excess soil. Shoot and root lengths were then measured and recorded. Growth promotion experiments were also conducted using rice (cultivar Rex). In these experiments rice seeds were surface disinfected for 1 hour in 4% NaOCl solution, then washed in sterile water. To inoculate seeds, surface disinfected seeds were soaked for 1 hour with continuous agitation in a suspension of *Pseudomonas fluorescens* Sandy LB4 at approximately 0.5 OD, 600 nm. Controls were surface disinfected seeds soaked in sterile water with agitation for 1 hour. 25 seeds for each treatment were planted in sterile soil in magenta boxes and incubated for 7 days under fluorescent lights at laboratory ambient temperature. Seedlings were removed from soil and root and shoot lengths determined.

Seed Germination and Seedling Root Architecture

Experiments were conducted to evaluate *Pseudomonas fluorescens* Sandy LB4 effects of seed germination and early seedling root architecture. In these experiments, seeds of *Poa annua* were surface disinfected for 45 mins as above then plated onto agarose media with without nutrients (Murashige and Skoogs basal medium) then monitored daily for 7 days for the parameters: percent germination, root development into agarose, root branching, and root and shoot lengths.

Disease Protection (Co-Culture Experiments)

To assess potential for disease protection bacteria *Pseudomonas fluorescens* Sandy LB4, *Pseudomonas* sp. West 9 and *Microbacterium oxydans* B2 were co-cultured on LBA with soil fungi, *Sclerotinia homeocarpa* or *Fusarium oxysporum* for 7 days. Formation of zones of inhibition were noted.

Damping Off Disease Control Experiment

To evaluate whether the *Phragmites* bacteria could protect seedlings from disease an experiment was set up using the damping off pathogen *Fusarium oxysporum*. In this experiment surface disinfected seeds of *Poa annua* were inoculated by soaking in a suspension (at approximately 0.5 OD, 600 nm) of strains Sandy LB4, West 9 or *Microbacterium oxydans* B2, then planted in magenta boxes containing previously sterilized soil that had been mixed with 10-mL of a conidial suspension of *Fusarium oxysporum*. Controls included treatment without bacterial or fungal treatments, and with fungus but without bacteria. Each treatment included 25 replicates. After 8 days and 15 days seedlings evident on the surface of the soil were counted. Also presence of fungal mycelium on the surface of soil was determined. To test for movement of the bacteria into soil a sterile probe was placed into soil between plants in each replicate, then the probe was streaked on a fresh Petri plant containing LB agar and incubated for 24 hours prior to examination.

Effects of *Phragmites* Bacteria on Growth of Competitor Plants

Dandelion (*Taraxacum officionalis*) was used to screen *Phragmites* microbes for any antagonism leading to increased mortality in the dandelion seedlings. Here dandelion seeds were rubbed against a nylon screen to remove awns and associated fibers. Seeds were then surface disinfected for 30 mins in 0.4% NaOCl, then rinsed in five changes of sterile water to remove residual chlorine. Seeds were used in a series of experiments.

Competitor Inhibition Experiment 1 (*Phragmites* Mixture 1)

Eleven seeds were placed onto the surface of agarose medium (0.7%) in Petri dishes. One drop of bacterial mixture 1 (including equal parts of *Microbacterium oxydans* B2, *Pseudomonas fluorescens* Sandy LB4, and *Pseudomonas* sp. West 9 at approximately OD 0.5, 600 nm) was applied to the surface of each seed (with 9 replica plates). Controls were moistened with sterile water only. Plates were then incubated at approximately 21° C. for two weeks in alternating light/dark conditions (10-hours light/14-hours dark). Seedlings were then examined to determine whether they were alive (light green) or dead (brown).

Competitor Inhibition Experiment 2 (*Phragmites* Mixture 1 and 2 in Soil)

In a second experiment dandelion seeds were cleaned of external fibers, surface disinfected as above and placed onto sterile soil in magenta boxes (10 seeds/treatment). Treatments included bacterial mixture 1 (as indicated above) and bacterial mixture 2 (including strains: *Pseudomonas* sp. WY6, *Pseudomonas* sp. Sandy LB6 *Pseudomonas* sp. Sandy Y8, *Pseudomonas* sp. RoLB13w, *Pantoea* sp. RoY12w). A control was not inoculated with *Phragmites* bacteria. To inoculate seeds with bacteria 2 mL of a bacterial suspension at approximately 0.5 OD, 600 nm was mixed into soil in magenta boxes. Seeds of *Poa annua* were also pre-moistened with bacterial suspension or water (control) then placed into soil and boxes incubated for four weeks under alternating light/dark conditions (10-hours light/14-hours dark) and 21° C. After four weeks seedlings were removed from soil, weighed, and root and shoot lengths determined (Table 4).

Competitor Inhibition Experiment 3 (Examination of Individual Bacterial Strains)

A screen was conducted using individual strains of the bacteria included in mixture 1 (as indicated above). In this preliminary individual screen, 14 disinfected dandelion seeds were placed on agarose media in Petri dishes. Seeds were inoculated as above with each bacterium, and control seeds were not inoculated. Three replica plates were made for each treatment and control. Plates were then incubated at approximately 21° C. for two weeks in alternating light/dark conditions (10-hours light/14-hours dark), after which mortality was assessed in each plate.

Competitor Inhibition Experiment 4 (*P. fluorescens* Sandy LB4)

A larger experiment was conducted using strain Sandy LB4. In this experiment dandelion seeds were cleaned and surface disinfected as above, then placed on 0.7% agarose in 38 Petri dishes (15 seeds/dish). Seeds on nineteen of the plates were inoculated using a suspension of Sandy LB4 as above, and the other nineteen were not inoculated. Plates were incubated for two weeks under the conditions of the previous experiment, after which seedling mortality was assessed.

Competitor Inhibition Experiment 5 (Effects on Seedlings of Curly Dock (*Rumex crispus*))

Seeds of locally collected curly dock were cleaned of bracts and associated wings, then surface disinfected for 40 minutes in 4% NaOCl. Ten seeds were then placed onto each of five Petri plates containing 0.7% agarose. Each seed was inoculated with a drop of bacterial suspension (strain Sandy LB4). Five control replica plates were prepared where seeds were not inoculated. Plates were incubated at approximately 21 C for one week in alternating light/dark conditions (10-hours light/14-hours dark) after which seedlings were stained using DAB and examined microscopically.

Competitor Inhibition Experiment 6 (Curly Dock in Soil)

A test was conducted in which 2 mL of individual bacteria (Sandy LB4, West 9, *M. oxydans* B2, or WY6 was mixed into previously sterilized soil in magenta boxes, then ten surface disinfected seeds of curly dock were placed into the soil 2-3 mm beneath surface. A control treatment was not inoculated with bacteria. After two weeks, the number of seedlings emerging from the soil surface was determined.

The following examples are provided to illustrate certain embodiments of the invention. They are not intended to limit the invention in any way.

Example I

Host Promotional Properties of Endophytic *Pseudomonas* Spp. from Seeds of Invasive Reed Grass (*Phragmites australis*)

This invention involves application of strains (e.g., Sandy LB4) of endophytic bacteria (belonging to genus *Pseudomonas*) for increasing growth of turf and forage grasses (*Agrostis* spp., *Poa* spp., *Festuca* spp., *Lolium* spp., *Cynodon* spp., *Zoysia* spp., *Koleria* spp., *Danthonia* sp.) and food grass crops (*Triticum aestivum, Oryza sativa, Zea maydis*), and suppress soil borne fungal diseases (e.g., damping off disease), and reduce vigor of seedlings of distantly-related weeds including *Taraxacum officinale* (dandelion) and curley dock (*Rumex crispus*). Each of the endophytes described herein (See Table 1) was obtained from seeds of the invasive grass *Phragmites australis*. For example, Sandy LB4 colonizes root meristems and enters into the cells of roots. This endophyte is unique in entering cells of the plant where it elicits production of reactive oxygen. Elicitation of reactive oxygen likely increases the resistance of the grass host to oxidative stress by stimulating the plant to up-regulate oxidative stress resistance genes. Sandy LB4 increases the growth of grass seedlings resulting in seedlings with larger root systems and larger shoots compared to seedlings without the bacterium. Sandy LB4 also moves from the plant roots out into the soil and colonizes mycelium of soil fungi suppressing growth of fungal pathogens resulting in reduced seedling disease. Sandy LB4 colonizes seedlings of non-grass competitor plants (dandelions and curly dock) and increases mortality of non-grass seedlings in laboratory experiments.

Application of the endophytic microbes obtained from *Phragmites australis* described herein to heterologous grass crops (e.g., turfgrasses, wheat, rice, *sorghum*, etc.) improves crop growth and reduces soil borne diseases and weeds. The endophytic bacteria listed in Table 1, including Sandy LB4, may be used alone or in combination in soil additives or seed treatments to grow crops with reduced agrochemical inputs. Widespread application of these endophytic bacteria commercially will enable decreased use of fertilizers, fungicides and herbicides on grass crops, resulting in reduced cost for expensive agrochemicals and reduced contamination of soil and water.

Isolates

Figure 2A:
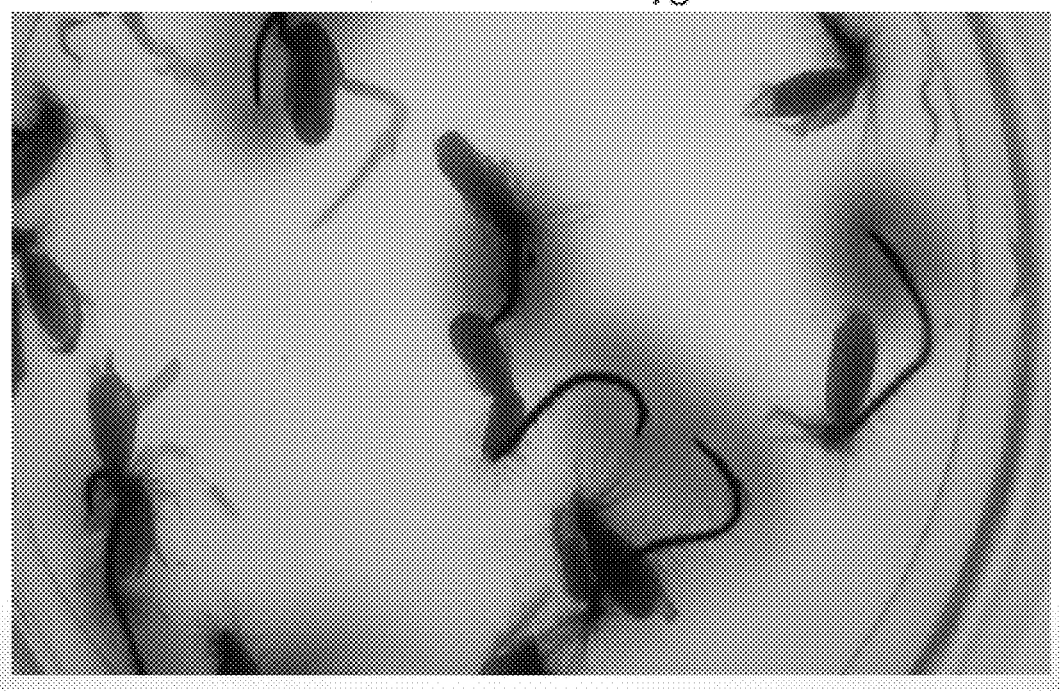
FIGS. 2A-2B.
Figure 2B:
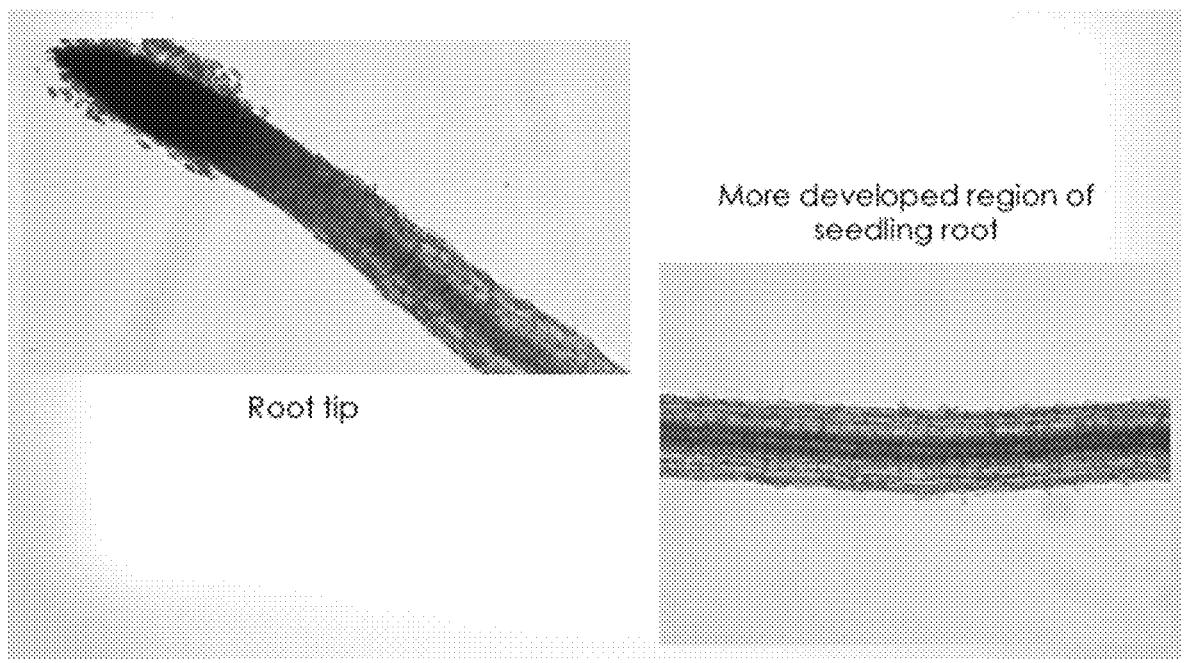

Sixteen bacterial isolates was obtained from the surfaces of *Phragmites* seeds. Of these, 12 were shown to belong in genus *Pseudomonas* based on 16S rDNA sequence data (Table 1). Two strains examined closely *Pseudomonas* sp. West 9 and *Pseudomonas fluorescens* Sandy LB4 were shown to become endophytic in the Bermuda grass seedlings (FIG. 1 and FIG. 2). These bacteria colonized root tip meristems and became intracellular in root cells, inducing formation of root hairs on seedling roots.

TABLE 1

Bacteria isolated from *Phragmites australis* seed surfaces

| Collection Site | Strain ID | UV | P[1] | Prot.[2] | Genus and Species | NRRL deposit # |
|---|---|---|---|---|---|---|
| Sandy Hook | Sandy LB4 | BF* | Y | Y | *P. fluorescens* | NRRL-B67308 |
| Sandy Hook | Sandy LB6 | LF | Y | N | *Pseudomonas* sp. | NRRL-B67484 |
| Sandy Hook | Sandy Y8 | LF | Y | N | *Pseudomonas* sp. | NRRL-B67896 |
| Robbinsville | RoY12 | NF | Y | N | *Pantoea* sp. | NRRL-B67898 |
| Robbinsville | RoLB13w | LF | Y | N | *Pseudomonas* sp. | NRRL-B67894 |
| West Windsor | WY9y | NF | Y | N | *Enterobacter* sp. | NRRL-B67485 |
| West Windsor | WY6 | LF | Y | N | *Pseudomonas* sp. | NRRL-XXXX |
| West Windsor | West 9 | LF | Y | N | *Pseudomonas* sp. | NRRL-B67307 |
| West Windsor | WY14 | NF | Y | Y | *Pseudomonas* sp. | NRRL-B67483 |
| South River | RiY3 | NF | Y | N | *Pseudomonas* sp. | NRRL-B67893 |
| Sandy Hook | SandyY7w | — | Y | N | *Pseudomonas* sp. | NRRL-B67895 |
| South River | RiLB4 | NF | Y | N | *Pantoea* sp. | NRRL-B67897 |
| Sandy Hook | SY1 | NF | Y | N | *Pseudomonas* sp. | NRRL-B67481 |
| Sandy Hook | SY5 | NF | Y | N | *Pseudomonas* sp. | NRRL-B67482 |
| West Windsor | WY9w | — | — | | *Pseudomonas* sp. | NRRL-XXXX |
| Cook Campus | B2 | | | | *Microbacterium oxydans* | NRRL-B67470 |

*BF = bright fluorescence; Lf = light fluorescence; NF = no fluorescence observed.
[1]Phosphorus solubilization, Y = yes; — = missing data
[2]Protease production based on milk agar clearing; Y = yes; N = no; — = missing data.
Partial 16S rDNA sequences for these strains from top to bottom are provided in SEQ ID NOS: 1, 2, 3, 6, 5, 12, 7, 10, 9, 4, 13, 14, 15, 16, and 8. Sequences are provided in Table 6.

Modes of Colonizing Bermuda Grass Seedling Roots

Figure 3A:
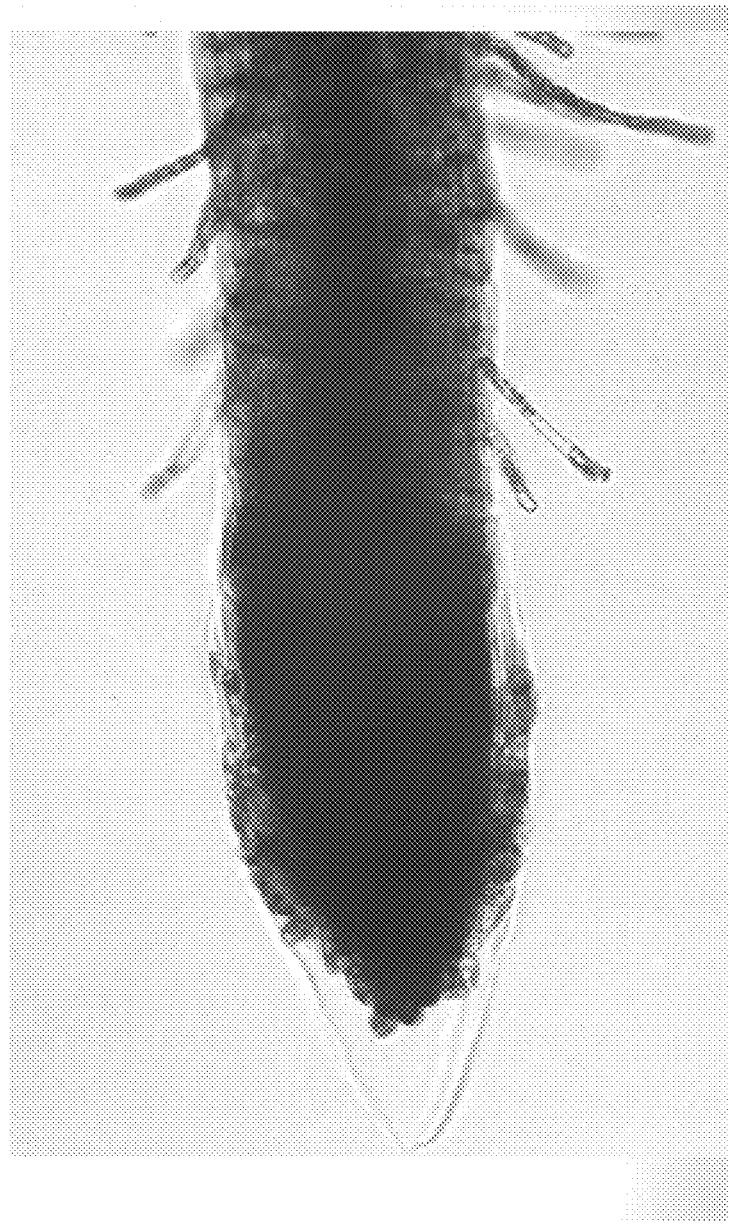
FIGS. 3A-3B.
Figure 3B:
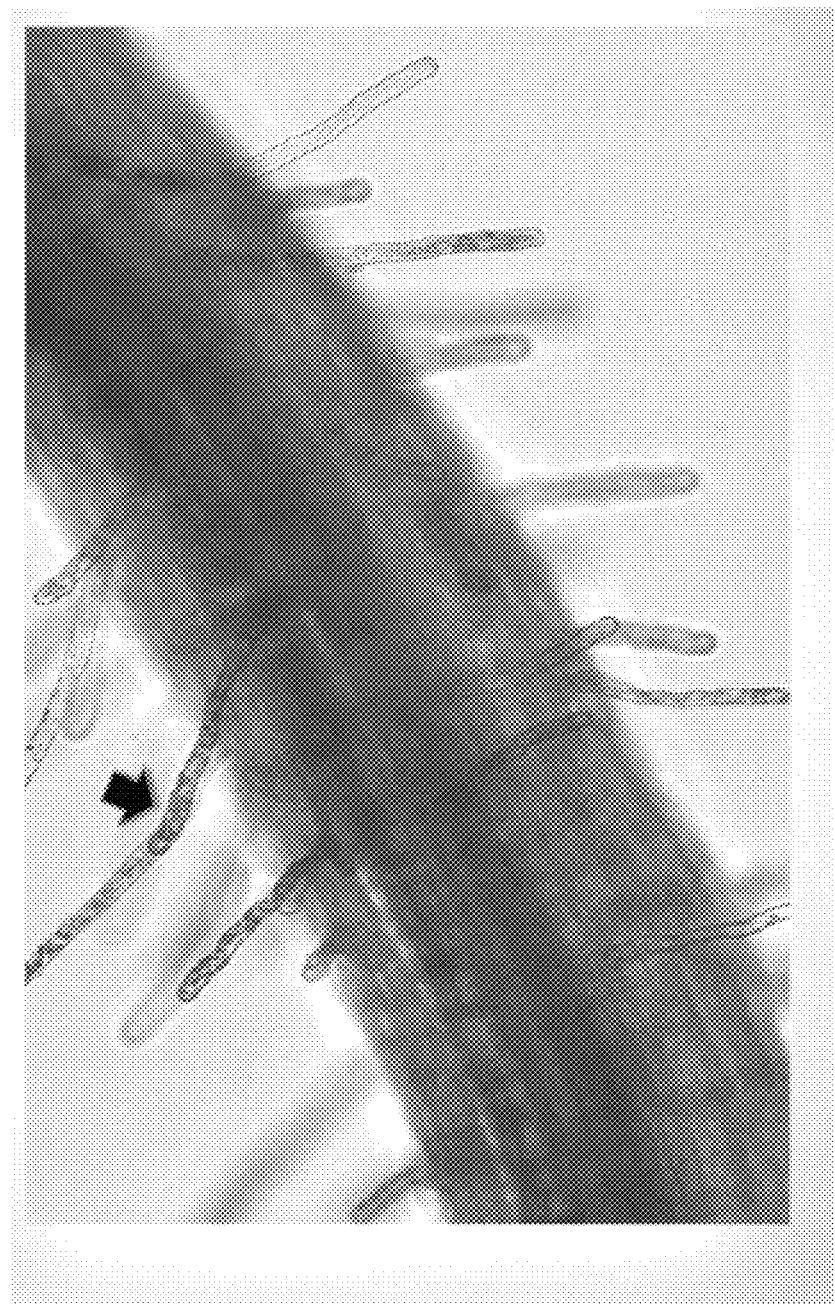
Figure 4A:
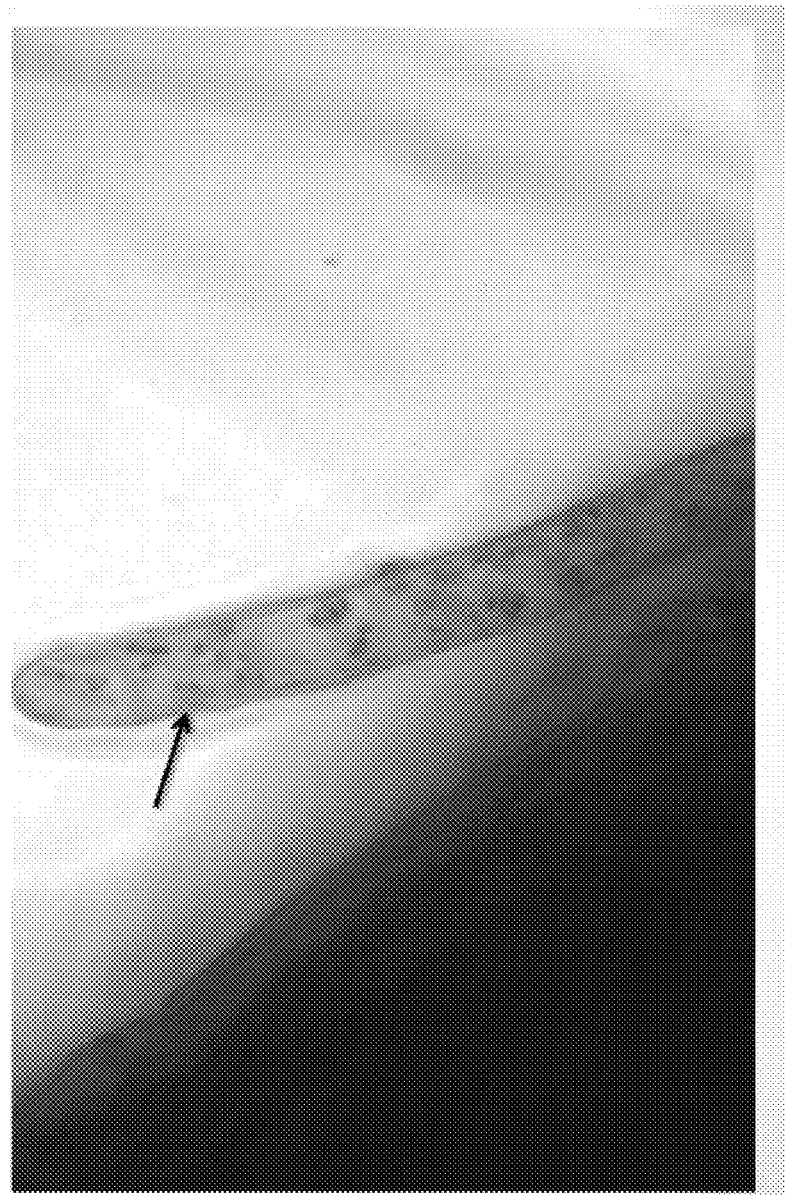
FIGS. 4A-4E.
Figure 4B:
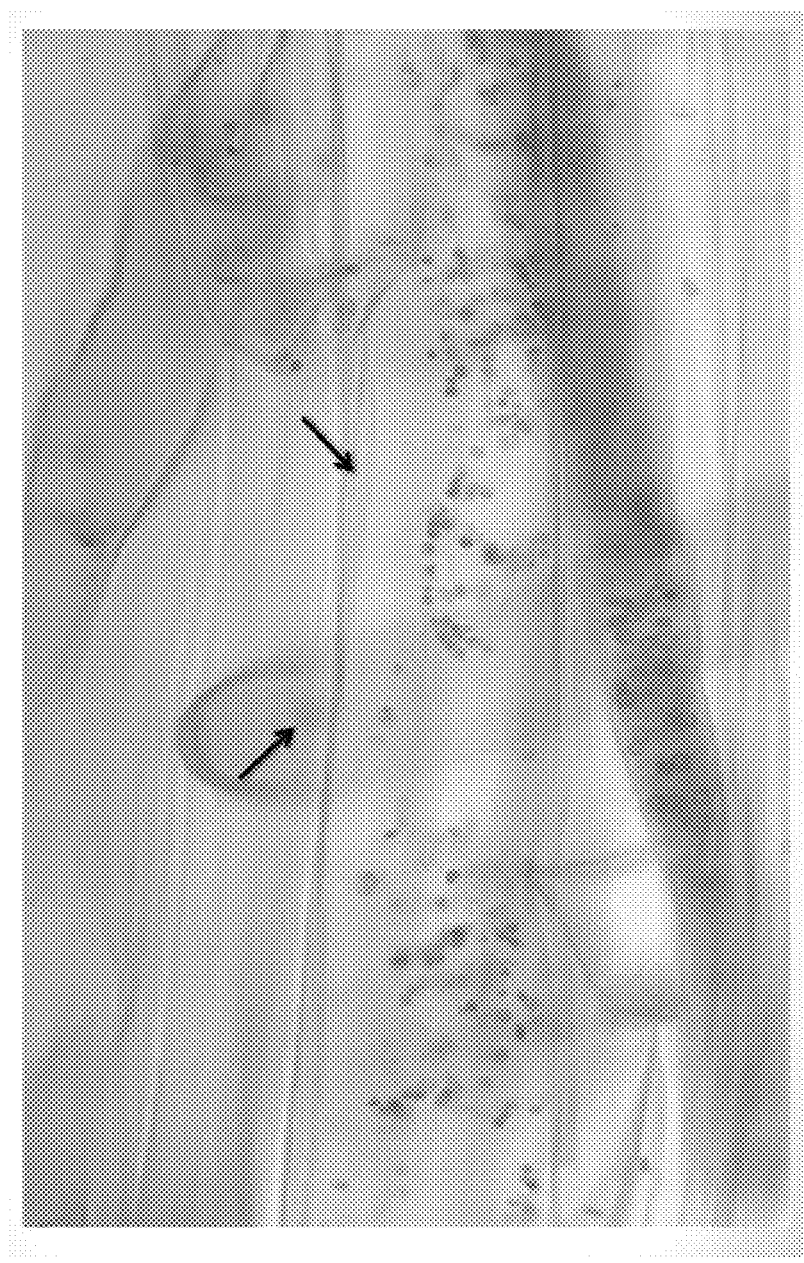
Figure 4C:
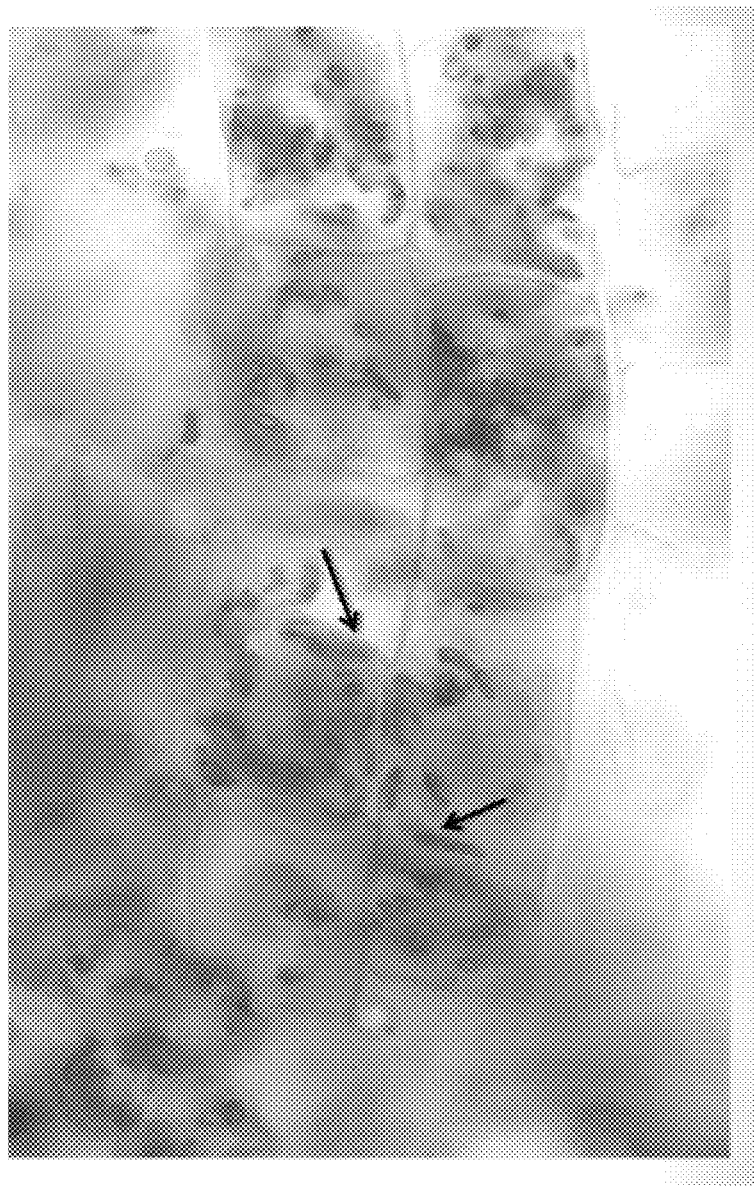
Figure 4D:
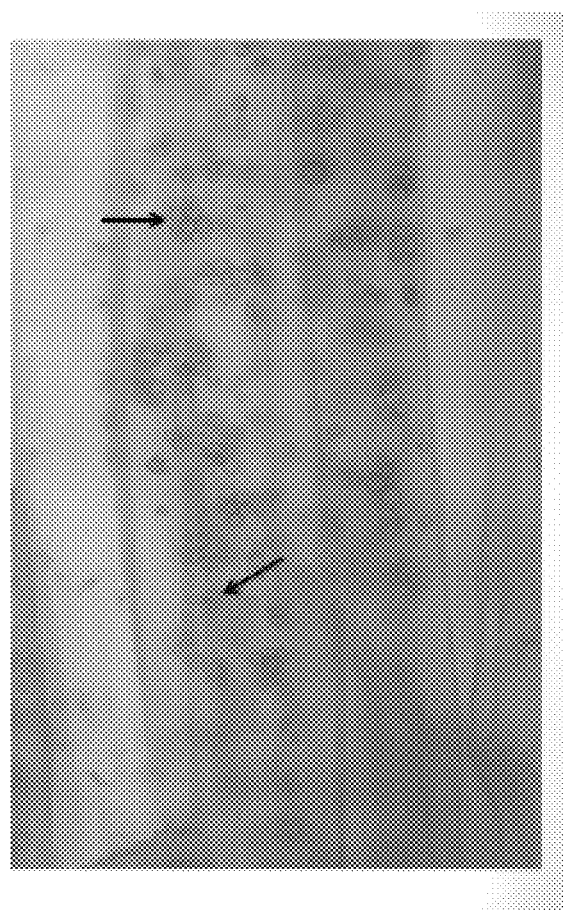
Figure 4E:
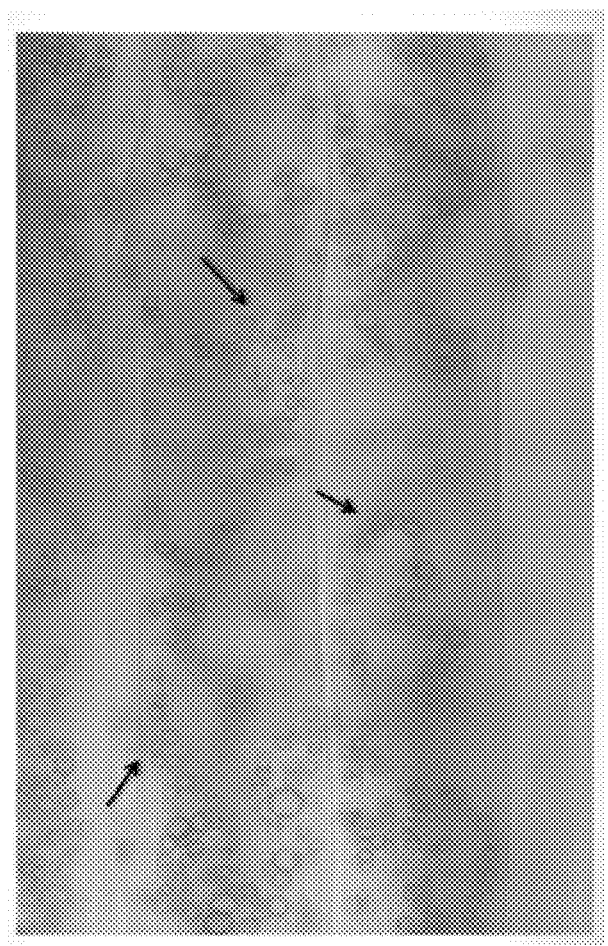
Figure 5A:
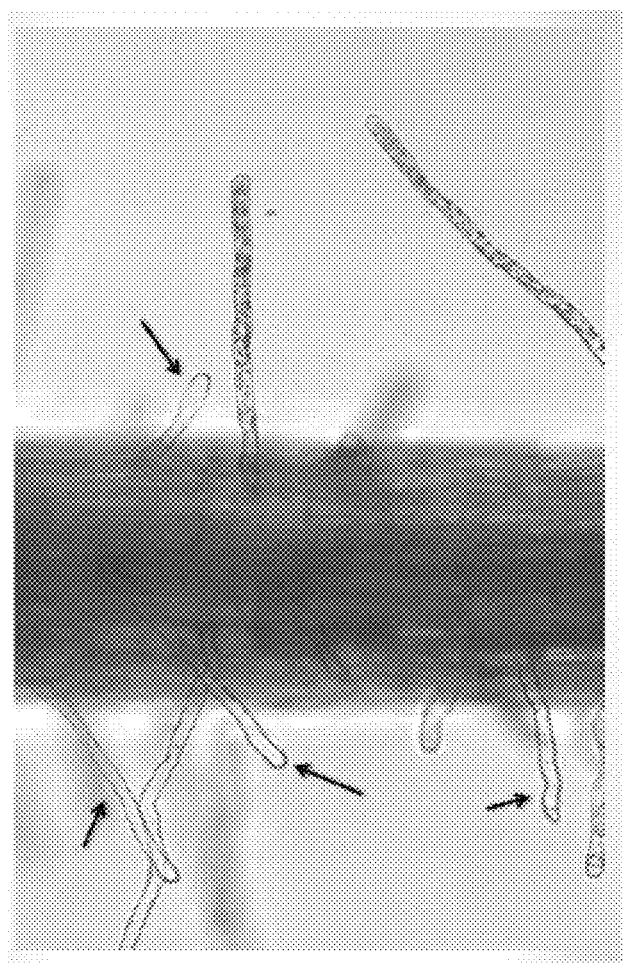
FIGS. 5A-5B.
Figure 5B:
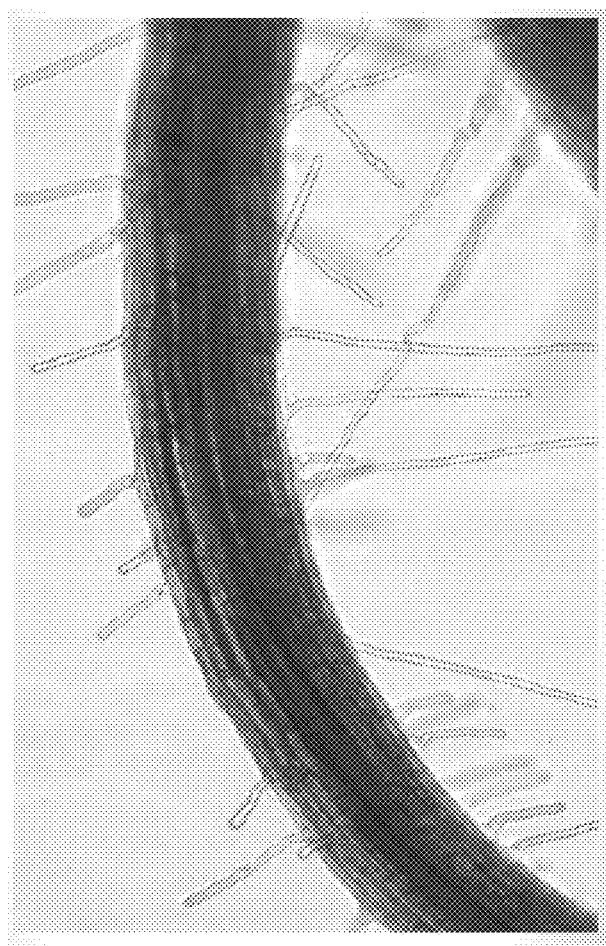

Several strains, including Sandy LB4 and West 9 were shown to enter root cells at the root meristem. Squash preparations of root tips showed presence of bacteria within meristematic cells. See FIG. 3A-3B. In older root cells, the spherical bacteria were seen to stain brown (positive indication of reactive oxygen) using the reactive oxygen stain DAB. Spherical bacterial L-forms were evident in root hairs and parenchyma cells (FIG. 4A-FIG. 4E) that comprised the main axis of the root. In older parts of the root the L-forms were seen to swell and the contents lacked protein as evident by failure to stain blue using the aniline blue counterstain (FIG. 5). In still older root parts, including root hairs and parenchyma, the internal bacterial inclusions were no longer evident. Seedlings derived from seeds that had not been inoculated with either Sandy LB4 or West 9 did not show presence of bacterial L-forms within root cells.

Plant Growth Promotion Capacity

*Pseudomonas fluorescens* Sandy LB4, *Pseudomonas* sp. West 9 and *Microbacterium oxydans* B2 were found to increase growth of *Poa annua* in the magenta box experiment. Roots and shoots of seedlings bearing these three bacteria were shown to be significantly longer than those without bacteria or inoculated with *Bosea thiooxidans* TBN (from Japanese knotweed; family Polygonaceae; Table 2). In the experiment where Sandy LB4 was applied to rice seeds, seedling shoot growth was increased 46% over seedlings without bacteria (Table 3). In general root and shoot lengths were significantly larger in inoculated seedlings than those of non-inoculated controls. In addition, roots of inoculated seedlings showed more adherent soil particles compared to non-inoculated seedling roots.

TABLE 2A

Growth promotion of *Poa annua* in soil for 37 days (15 plants in each treatment)

| Treatment | Shoot length (mm)* | Root length (mm) |
|---|---|---|
| No bacteria | 88.87 ± 23.53$^a$ | 17.27 ± 8.59$^a$ |
| TBN | 86.2 ± 32.35$^a$ | 13.73 ± 5.01$^a$ |
| Sandy LB4 | 122.33 ± 27.38$^b$ | 23.8 ± 8.54$^b$ |
| West 9 | 119.33 ± 20.43$^b$ | 27.33 ± 14.56$^b$ |
| *Microbacterium oxydans* B2 | 113.73 ± 25.41$^b$ | 20.87 ± 6.79$^{a,b}$ |

*Data is given as mean ± standard deviation. Means followed by the same letter within a column are not significantly different according to the Duncan multiple range test ($p < 0.05$).

TABLE 2B

Growth promotion of Bermuda grass (*Cynodon* spp.)

| Endophytes (Bacteria) | Geotropic response (%) | Root length (cm) | Root hairs and branching* | Shoot length (cm) | IAA test |
|---|---|---|---|---|---|
| Control | 35 | 1.5-2.0 | + | 1.5-2.0 | — |
| 1. West9 | 35 | 1.5-2.0 | +++ | 1.5-2.0 | NA |
| 2. Sandy LB4 | 50 | 2.0-3.0 | +++ | 1.5-2.5 | — |
| 3. *Microbacterium oxydans* B2 | 40 | 1.0-1.5 | + | 1.5-2.0 | NA |
| 4. SY1 | 40 | 2.0-3.0 | +++ | 1.5-2.5 | — |
| 5. Sandy LB6 | 60 | 2.0-3.0 | +++ | 1.5-2.5 | — |

TABLE 3

Rice seedling development with and without the indicated endophytic bacteria isolate

| Endophytes (Bacteria) | Geotropic response (%) | Root length (cm) | Root hairs and branching* | Shoot length (cm) | Phosphate solubilization |
|---|---|---|---|---|---|
| Control | 10 | 1.0-2.0 | + | 1.0-2.0 | − |
| 1. West9 | 20 | 2.0-3.0 | ++ | 2.0-2.5 | + |
| 2. Sandy LB4 | 40 | 2.0-3.0 | +++ | 2.0-3.0 | + |
| 3. *Microbacterium oxydans* B2 | 20 | 2.0-3.0 | ++ | 2.0-2.5 | + |
| 4. SY1 | 25 | 2.0-2.5 | +++ | 2.0-2.5 | + |
| 5. SY5 | 10 | 1.0-2.0 | No | 1.0-2.0 | NA |
| 6. Sandy LB6 | 25 | 2.0-3.0 | ++ | 2.0-3.0 | + |
| 7. RiY3 | 0.0 | 1.0-1.5 | No | 0.5-1.5 | NA |
| 8. ROLB13y | 10 | 1.0-1.5 | No | 0.5-1.5 | NA |

Seed Germination Rate and Root Architecture

Figure 6A:
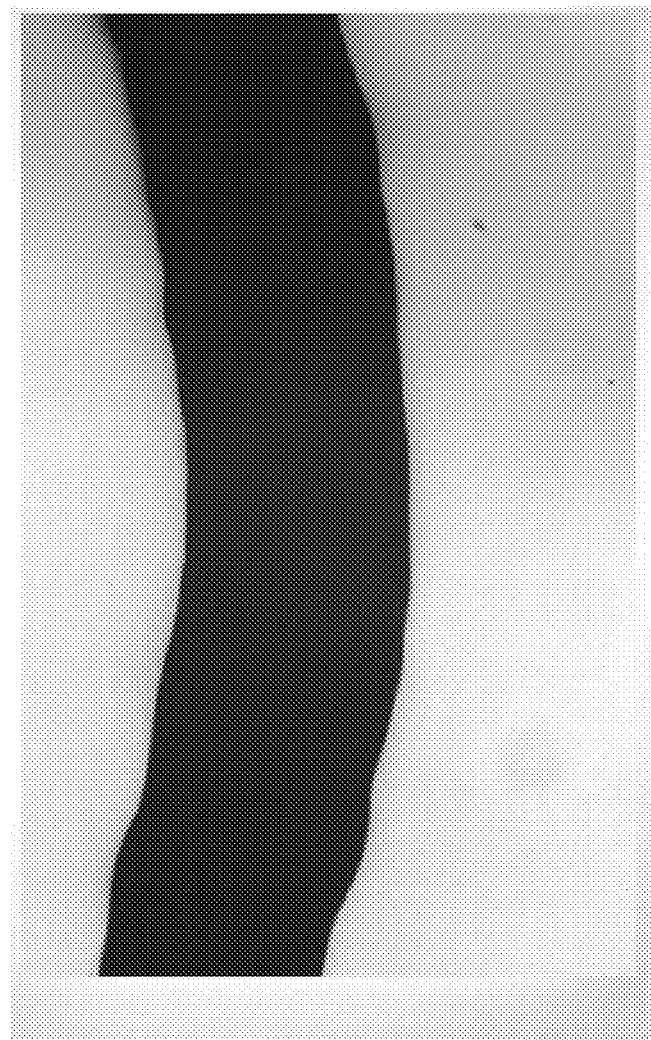
FIGS. 6A-6C.
Figure 6B:
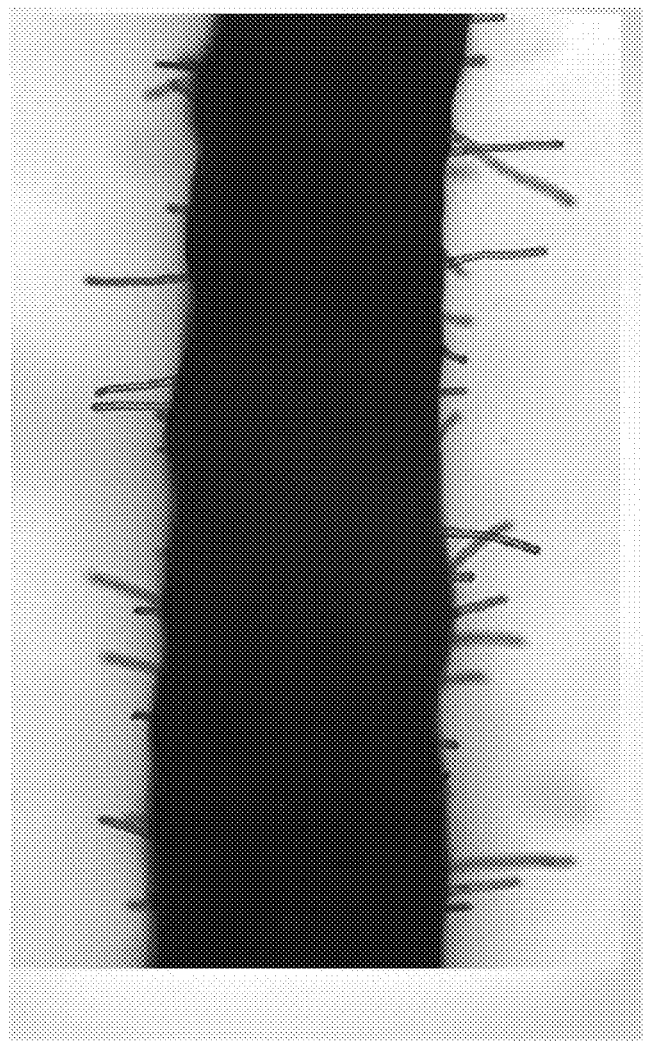
Figure 6C:
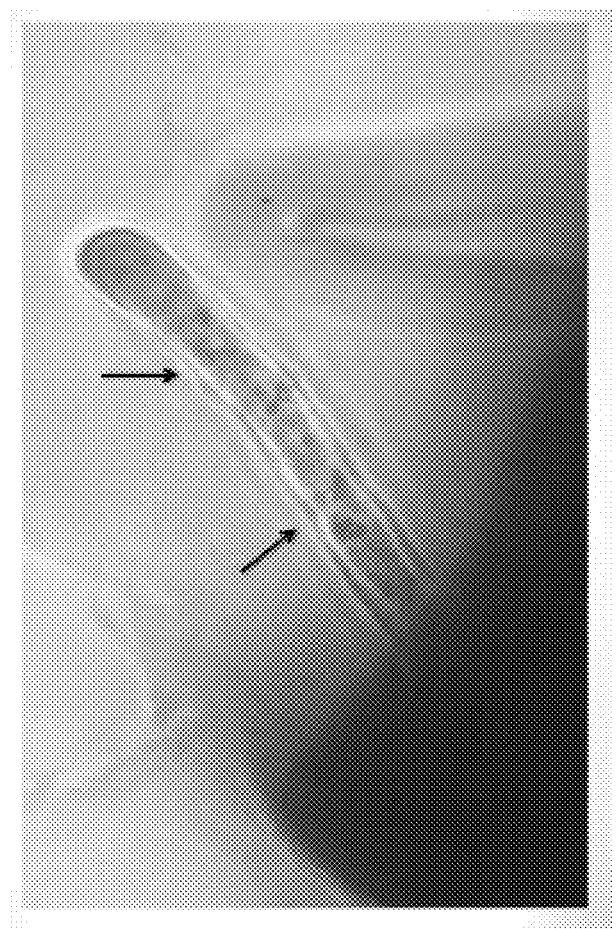
Figure 7A:
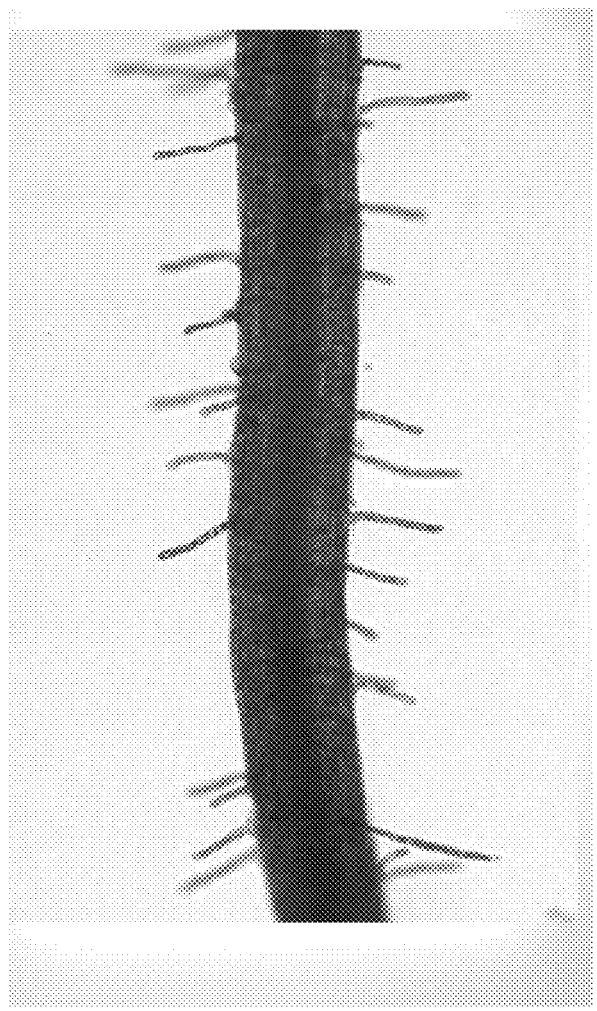
FIGS. 7A-7B.
Figure 7B:
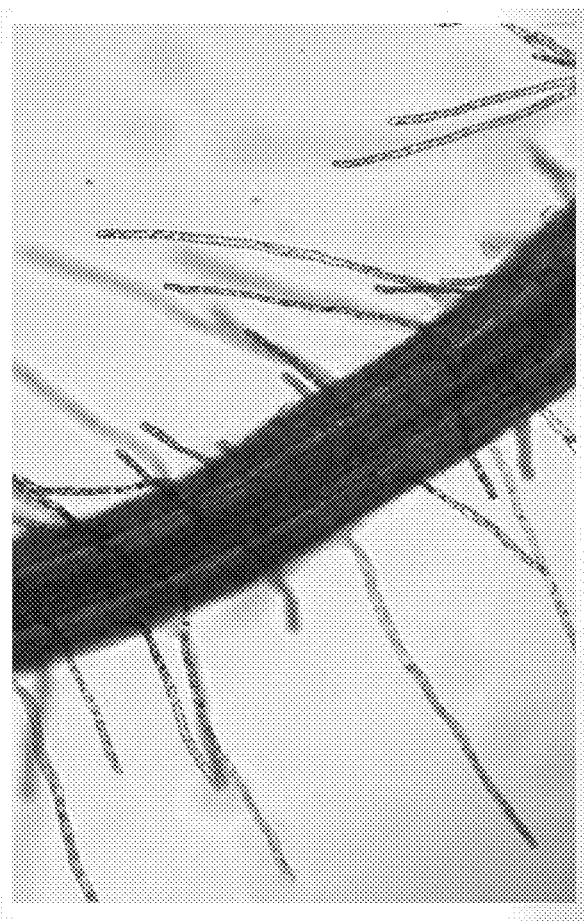

In the germination and root growth study where we used axenic *Poa annua* to determine bacterial effects on seeds and seedlings, we found that the germination rate was only slightly increased in seeds bearing Sandy LB4. However, there was a slightly greater tendency for roots bearing the bacterium to branch compared to roots without the bacterium (FIG. 6). In the agarose medium roots bearing the bacterium were also seen to more frequently grow downward into the agarose medium than roots without the bacterium. It is notable that in seedlings grown on agarose containing Murashige and Skoogs nutrient base, the majority of the roots tended to grow downward into the medium (Table 4).

TABLE 4

*Poa annua* germination and growth with *Phragmites* bacterium Sandy LB4 over a 1-week period.

| | Total GERM | % GERM | Roots Down | Roots Up | $2^{nd}$ root | $3^{rd}$ root | Shoot Avg. | Root Avg. |
|---|---|---|---|---|---|---|---|---|
| Agarose | | | | | | | | |
| No bacteria | 117 | 90 | 30 | 87 | 100 | 58 | 18 | 16 |
| Sandy LB4 | 123 | 95 | 54 | 68 | 103 | 71 | 21 | 12 |
| MS | | | | | | | | |
| No bacteria | 118 | 91 | 116 | 0 | 67 | 1 | 26 | 12 |
| Sandy LB4 | 122 | 94 | 116 | 4 | 78 | 6 | 24 | 13 |

Production of Fungal Inhibitors

Inhibition zones were evident in co-culture experiments, where West 9 and Sandy LB4 were cultured with *Sclerotinia homeocarpa* and *Fusarium oxysporum* and seen to inhibit them in culture. *Microbacterium oxydans* B2 did not produce inhibitory substances in culture. Another endophytic bacteria, SY1, also produced fungal inhibitors as described further below.

Damping Off Disease Protection

In the experiment evaluating capacity of *Phragmites* bacteria to protect *P. annua* seedlings from damping off caused by *Fusarium oxysporum*, we showed that the least damping off was seen in the pathogen and bacterial free treatment with 23 seedlings surviving after 15 days. After 15 days Sandy LB4 showed the highest level of protection with 20 seedlings surviving; followed by West 9 with 16 seedlings surviving, *Microbacterium oxydans* B2 with 15 seedlings surviving, and the pathogen+no bacterium treatment with 12 seedlings surviving. SYI also effectively inhibited fungal growth as described below.

Effects of *Phragmites* Bacteria on Growth of Seedlings of Competitor Species

In competitor inhibition experiment 1 we showed that a mixture of *Phragmites* bacteria (including *Microbacterium oxydans* B2, *Pseudomonas* sp. West 9 and *Pseudomonas fluorescens* Sandy LB4) increased mortality in dandelion seedlings compared to the non-inoculated control with the difference being statistically significant at the 5% level of significance in the Student's t-test. The bacterial mixture gave an 83.4±15.7% mortality compared to the axenic control at 16.4±22.8% mortality.

In competitor inhibition experiment 2 conducted in soil in magenta boxes we found that inoculation of soil with bacterial mixture 1 (including Sandy LB1, West 9 and *Microbacterium oxydans* B2) resulted seedlings that were significantly smaller in terms of weight, and shoot and root lengths than those of non-inoculated seedlings or those grown in soil containing *Phragmites* bacterial mixture 2 containing five other isolates (Table 5).

TABLE 5

Dandelion seedling growth inhibition in
soil by *Phragmites* bacterial mixtures

| Treatment | Seedling mass Wet weight (mg) | Shoot length (mm) | Root length (mm) |
|---|---|---|---|
| No bacteria | 27.03 ± 9.54*[a] | 42.44 ± 12.6[a] | 40 ± 17.11[a] |
| Mix 1 | 14.91 ± 8.71[b] | 23.88 ± 11.86[b] | 14.63 ± 5.21[b] |
| Mix 2 | 26.36 ± 6.78[a] | 40.89 ± 10.71[a] | 43.33 ± 19.55[a] |

*Data given as means ± standard deviation. Within columns means followed by the same letter are not statistically different according to the Duncan multiple range test ($p < 0.05$).

Identification of Strains Showing Dandelion Seedling Inhibition

Figure 9A:
FIGS. 9A-9B.
Figure 9B:
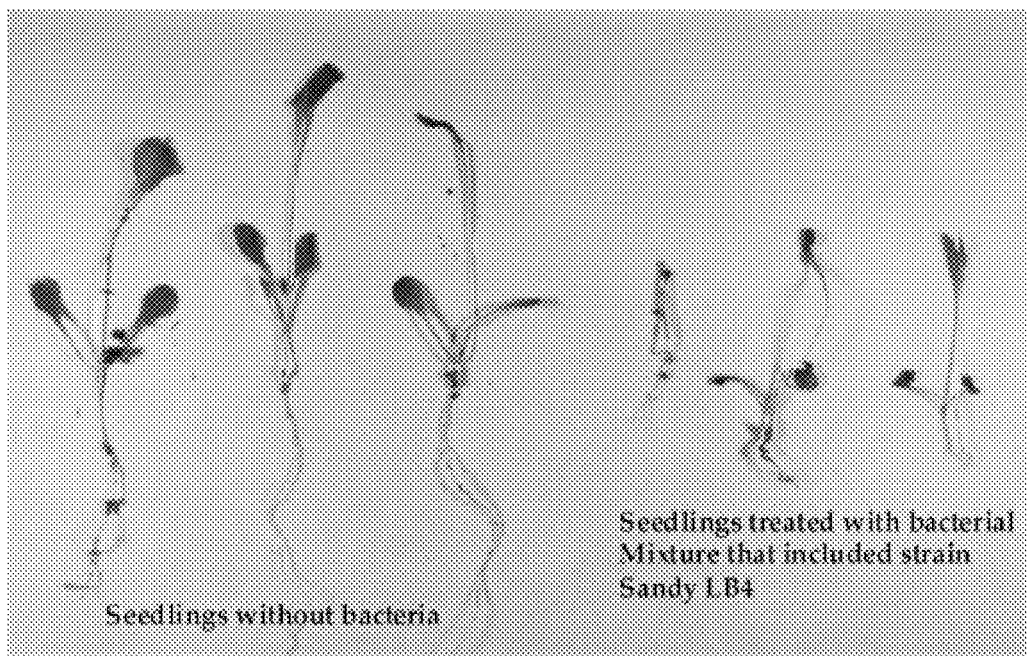

In competitor inhibition experiment 3, *Pseudomonas fluorescens* Sandy LB4, *Pseudomonas* sp. West 9 and *Microbacterium oxydans* B2 were tested for their effect on mortality of dandelion seedlings on agarose (FIG. 9). In this test the most potent bacterium for increasing mortality of dandelion seedlings was Sandy LB4 (71%)>*Microbacterium oxydans* B2 (35%)>West 9 (31%)>no bacterium control (23%). On the basis of this test we concluded that Sandy LB4 was the most potent of the bacteria increasing mortality in dandelion seedlings and a larger study (Competitor inhibition experiment 4) was set up to gather statistical data for effect of Sandy LB4 on dandelion seedling mortality. In the larger study a statistically significant ($p<0.05$ in student's t-test) increased mortality of 71.1±15.3% was shown for Sandy LB4-inoculated seedlings compared to only 6.8±7.4% for the non-inoculated control treatment.

Figure 8A:
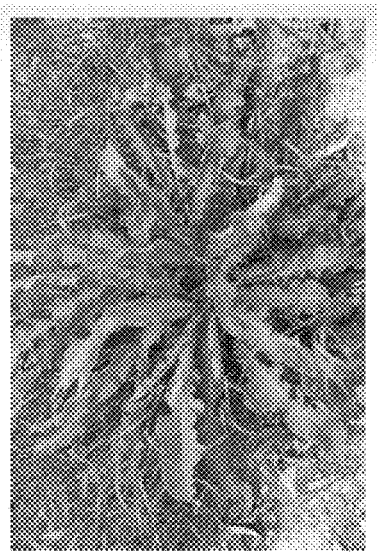
FIGS. 8A-8C.
Figure 8B:
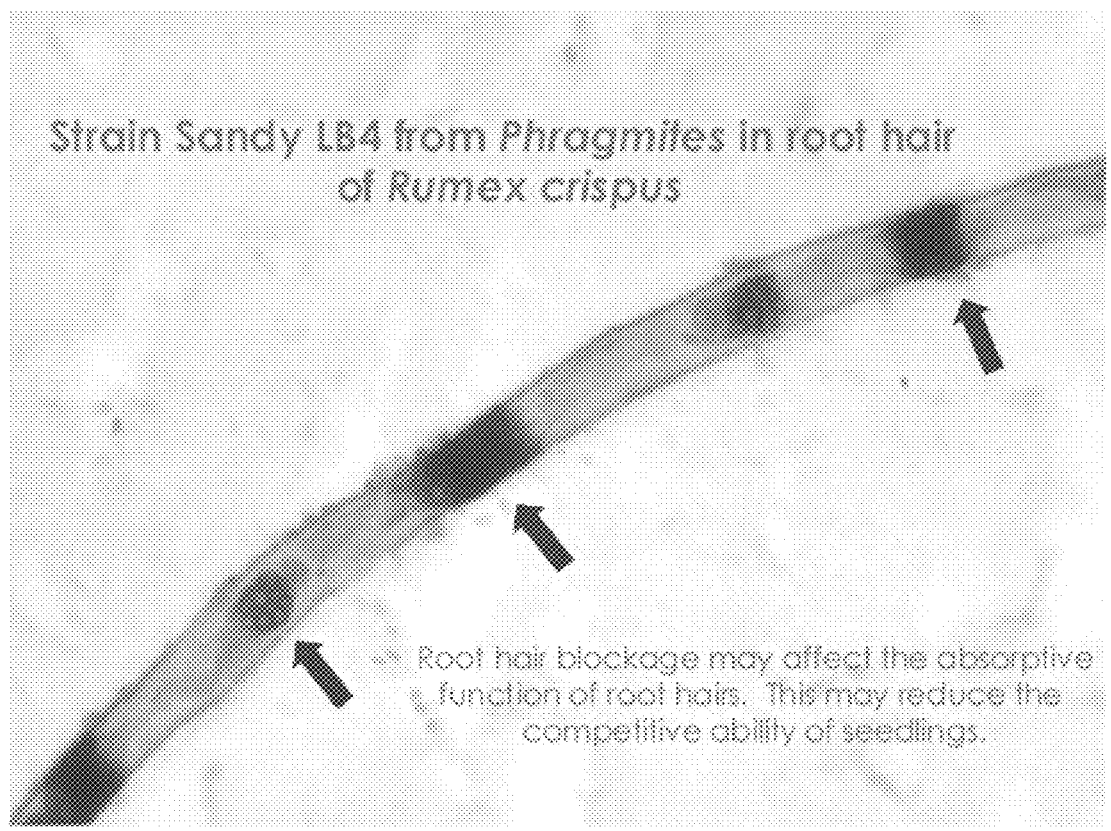
Figure 8C:
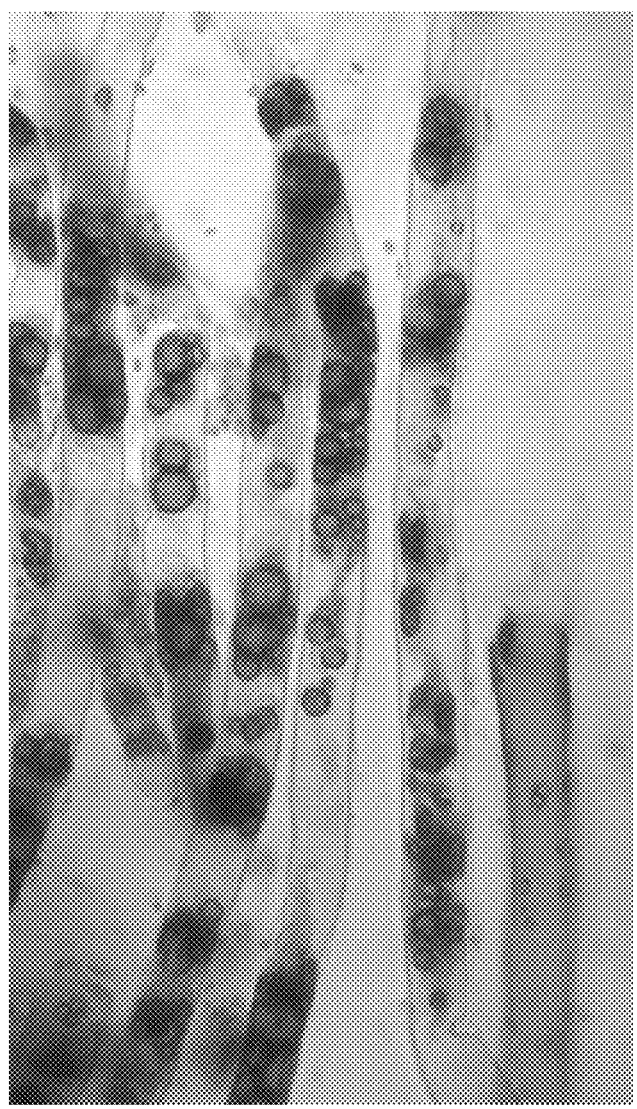

Effects of *Pseudomonas fluorescens* Sandy LB4 on Curly Dock (*Rumex crispus*) Seedlings In competitor inhibition experiment 5 we evaluated the colonization of seedlings of *Rumex crispus* by Sandy LB4. Here we found that Sandy LB4 actively colonized seedlings, inducing root hair development in the inoculated seedlings. Staining the seedlings using the reactive oxygen stain DAB and microscopic examination of roots showed that root hairs appeared to be occluded by large dark clusters of swollen degrading L-form bacteria (FIG. 8). In competitor inhibition test 6 in soil we showed that curly dock seedling emergence was: no bacterium treatment (7 seedlings)>West 9 (3 seedlings)>*Microbacterium oxydans* B2 (2 seedlings)>Sandy LB4 (0 seedlings).

Fungal Disease Protection in Rice (*Oryza sativa*) Seedlings by Growth Promoting Seed Associated Endophytic Bacteria from Invasive *Phragmites australis*

As discussed at length above, non-cultivated plants carry endophytes that may be used to enhance development and disease resistance of desirable crops. During seedling establishment, rice may be infected by fungal pathogens. Species of *Fusarium* and *Pythium* cause rice seed rot during germination. *Fusarium* blight in rice seedlings is common and affects seedling development.

We found that three bacteria, including *Pseudomonas fluorescens* (Sandy LB4), *Pseudomonas* sp. (Sandy LB6) and *Pseudomonas* sp. (SY1) promoted seedling development, including enhancement of root and shoot growth, and modulation of root hair formation in rice and Bermuda grass. The results with Sandy LB4 and rice are provided above in Table 3. Bacteria were positive for phosphate solubilization. Another bacteria, *Pseudomonas* sp. (SY1) protected rice and Bermuda grass seedlings from *Fusarium* infection. In co-culture experiments, strain SY1 inhibited fungal pathogens with 85.71% growth inhibition of *F. oxysporum*, 86.33% growth inhibition of *Curvularia* sp. and 82.14% growth inhibition of *Alternaria* sp. Seedlings of Bermuda grass and rice treated with bacteria were found much less infected by *F. oxysporum* in comparison to nontreated controls. Bacteria appeared to actively degrade fungal mycelia. Metabolite products of strain SY1 were also found to inhibit fungal growth on nutrient media. *Pseudomonas* sp. (SY1) was found to produce inhibitory volatiles. MALDI-TOF analysis revealed that SY1 produces antifungal lipopeptides of the fengycin family which appear to be responsible for the antifungal activity of SY1.

TABLE 6

Exemplary partial 16S rDNA and SEQ ID NOS: for strains described herein

```
Sandy LB4 (Pseudomonas fluorescens deposited as NRRL-B67308)
TAGATACCCTGGTAGTCCACGCCGTAACGATGTCAACTAGCCGTTGGGAGCCTTGAGCTCTTAGTGGCGCAGCTAACGCA
TTAAGTTGACCGCCTGGGGAGTACGGCCGCAAGGTTAAAACTCAAATGAATTGACGGGGGCCCGCACAAGCGGTGGAGCA
TGTGGTTTAATTCGAAGCAACGCGAAGAACCTTACCAGGCCTTGACATCCAATGAACTTTCTAGAGATAGATTGGTGCCT
TCGGGAACATTGAGACAGGTGCTGCATGGCTGTCGTCAGCTCGTGTCGTGAGATGTTGGGTTAAGTCCCGTAACGAGCGC
AACCCTTGTCCTTAGTTACCAGCACGTTATGGTGGGCACTCTAAGGAGACTGCCGGTGACAAACCGGAGGAAGGTGGGGA
TGACGTCAAGTCATCATGGCCCTTACGGCCTGGGCTACACACGTGCTACAATGGTCGGTACAAAGGGTTGCCAAGCCGCG
AGGTGGAGCTAATCCCATAAAACCGATCGTAGTCCGGATCGCAGTCTGCAACTCGACTGCGTGAAGTCGGAATCGCTAGT
AATCGCGAATCAGAATGTCGCGGTGAATACGTTCCCGGGCCTTGTACACACCGCCCGTCACACCATGGGAGTGGGTTGCA
CCAGAAGTAGCTAGTTTAACCTTCGGG (SEQ ID NO: 1)

Sandy LB6 (Pseudomonas sp. deposited as NRRL-B67484)
GTCCTTAGTTACCAGCACGTTATGGTGGGCACTCTAAGGAGACTGCCGGTGACAAACCGGAGGAAGGTGGGGATGACGTC
AAGTCATCATGGCCCTTACGGCCTGGGCTACACACGTGCTACAATGGTCGGTACAGAGGGTTGCCAAGCCGCGAGGTGGA
GCTAATCTCACAAAACCGATCGTAGTCCGGATCGCAGTCTGCAACTCGACTGCGTGAAGTCGGAATCGCTAGTAATCGCG
AATCAGAATGTCGCGGTGAATACGTTCCCGGGCCTTGTACACACCGCCCGTCACACCATGGGAGTGGGTTGCACCAGAAG
TA (SEQ ID NO: 2)

Sandy Y8 (Pseudomonas sp. deposited as NRRL-B67896)
CTACTTCTGGTGCAACCCACTCCCATGGTGTGACGGGCGGTGTGTACAAGGCCCGGGAACGTATTCACCGCGACATTCTG
ATTCGCGATTACTAGCGATTCCGACTTCACGCAGTCGAGTTGCAGACTGCGATCCGGACTACGATCGGTTTTGTGAGATT
AGCTCCACCTCGCGGCTTGGCAACCCTCTGTACCGACCATTGTAGCACGTGTGTAGCCCAGGCCGTAAGGGCCATGATGA
CTTGACGTCATCCCCACCTTCCTCCGGTTTGTCACCGGCAGTC (SEQ ID NO: 3)

RiY3 (Pseudomonas sp. deposited as NRRL-B67893)
TTTGACGTTACCGACAGAATAAGCACCGCTAACTCTGTGCCAGCAGCCGCGGTAATACAGAGGGTGCAAGCGTTAATCG
GAATTACTGGGCGTAAAGCGCGCGTAGGTGGTTTGTTAAGTTGGATGTGAAAGCCCCGGGCTCAACCTGGGAACTGCATC
CAAAACTGGCAAGCTAGAGTACGGTAGAGGGTGGTGGAATTTCCTGTGTAGCGGTGAAATGCGTAGATATAGGAAGGAAC
ACCAGTGGCGAAGGCGACCACCTGGACTGATACTGACACTGAGGTGCGAAAGCGTGGGGAGCAAACAGGATTAGATACCC
```

TABLE 6-continued

Exemplary partial 16S rDNA and SEQ ID NOS: for strains described herein

TGGTAGTCCACGCCGTAACGATGTCAACTAGCCGTTGGAATCCTTGAGATTTTAGTGGCGCAGCTAACGCATTAAGTTGA
CCGCCTGGGGAGTACGGCCGCAAGGTTAAAACTCAAATGAATTGACGGGGGCCCGCACAAGCGGTGGAGCATGTGGTTTA
ATTCGAAGCAACGCGAAGAACCTTACCGGCCTTGACATGCAGAGAACTTTCCAGAGATGGATGG (SEQ ID NO: 4)

RoLB13w (Pseudomonas sp. deposited as NRRL-B67894)
TGGGAACTGCATCCAAAACTGGCAAGCTAGAGTACGGTAGAGGGTGGTGGAATTTCCTGTGTAGCGGTGAAATGCGTAGA
TATAGGAAGGAACACCAGTGGCGAAGGCGACCACCTGGACTGATACTGACACTGAGGTGCGAAAGCGTGGGGAGCAAACA
GGATTAGATACCCTGGTAGTCCACGCCGTAAACGATGTCAACTAGCCGTTGGAATCCTTGAGATTTTAGTGGCGCAGCTA
ACGCATTAAGTTGACCGCCTGGGGAGTACGGCCGCAAGGTTAAAACTCAAATGAATTGACGGGGGCCCGCACAAGCGGTG
GAGCATGTGGTTTAATTCGAAGCAACGCGAAGAACCTTACCAGGCCTTGACATGCAGAGAACTTTCCAGAGATGGATTGG
TGCCTTCGGGAACTCTGACACAGGTGCTGCATGGCTGTCGTCAGCTCGTGTCGTGAGAGTTGGGTTAAGTCCCGTAACG
AGCGCAACCCTTGTCCTTAGTTACCAGCACGTTATGGTGGGCACTCTAAGGAGACTGCCGGTGACAAACCGGAGGAAGGT
GGGGATGACGTCAAGTCATCATGGCCCTTACGGCCTGGGCTACACACGTGCTACAATGGTCGGTACAGAGGGTTGCCAAG
CCGCGAGGTGGAGCTAATCTCACAAAACCGATCGTAGTCCGGATCGCAGTCTGCAACTCGACTGCGTGAAGTCGGAATCG
CTAGTAATCGCGAATCAGAATGTCGCGGTGAATACGTTCCCGGGCCTTGTACACACCGCCCGTCACACCATGGGAGTGGG
TTGCACCAGAAG (SEQ ID NO: 5)

RoY12 (Pantoea sp. deposited as NRRL-B67898)
AAGCTCGTGTTGTGAAATGTTGGGTTAAGTCCCGCAACGAGCGCAACCCTTATCCTTTGTTGCCAGCGATTCGGTCGGGA
ACTCAAAGGAGACTGCCGGTGATAAACCGGAGGAAGGTGGGGATGACGTCAAGTCATCATGGCCCTTACGAGTAGGGCTA
CACACGTGCTACAATGGCGCATACAAAGAGAAGCGACCTCGCGAGAGCAAGCGGACCTCACAAAGTGCGTCGTAGTCCGG
ATCGGAGTCTGCAACTCGACTCCGTGAAGTCGGAATCGCTAGTAATCGTGGATCAGAATGCCACGGTGAATACGTTCCCG
GGCCTTGTACACACCGCCCGTCACACCATGGGAGTGGGTTGCAAAAGAAGTA (SEQ ID NO: 6)

WY6 (Pseudomonas sp. deposited as NRRL-___)
GAAGGTTAGACTAGCTACTTCTGGTGCAACCCACTCCCATGGTGTGACGGGCGGTGTGTACAAGGCCCGGGAACGTATTC
ACCGCGACATTCTGATTCGCGATTACTAGCGATTCCGACTTCACGCAGTCGAGTTGCAGACTGCGATCCGGACTACGATC
GGTTTTGTGGGATTAGCTCCACCTCGCGGCTTGGCAACCCTCTGTACCGACCATTGTAGCACGTGTGTAGCCCAGGCCGT
AAGGGCCATGATGACTTGACGTCATCCCCACCTTCCTCCGGTTTGTCACCGGCAGTCTCCTTAGAGTGCCCACCATCACG
TGCTGGTAACTAAGGACAAGGGTTGCGCTCGTTACGGGACTTAACCCAACATCTCACGACACGAGCTGACGACAGCCATG
CAGCACCTGTCTCAATGTTCCCGAAGGCACCAATCCATCTCTGGAAAGTTCATTGGATGTCAAGGCCTGGTAAGGTTCTT
CGCGTTGCTTCGAATTAAAACACATGCTCCACCGCTTGTGCGGGCCCCCGTCAATTCATTTGAGTTTTAACCTTGCGGCC
GTACTCCCCAGGCGGTCAACTTAATGCGTTAGCTGCGCCACTAAGAGCTCAAGGCTCCCAACGGCTAGTTGACATCGTTT
ACGGCGTGGACTACCAGGGTATCTAATCCTGTTTGCTCCCCACGCTTTCGCACCTCA (SEQ ID NO: 7)

WY9w (Pseudomonas sp. deposited as NRRL-___)
CTTCTGGTGCAACCCACTCCCATGGTGTGACGGGCGGTGTGTACAAGGCCCGGGAACGTATTCACCGCGACATTCTGATT
CGCGATTACTAGCGATTCCGACTTCACGCAGTCGAGTTGCAGACTGCGATCCGGACTACGATCGGTTTTGTGGGATTAGC
TCCACCTCGCGGCTTGGCAACCCTCTGTACCGACCATTGTAGCACGTGTGTAGCCCAGGCCGTAAGGGCCATGATGACTT
GACGTCATCCCCACCTTCCTCCGGTTTGTCACCGGCAGTCTCCTTAG (SEQ ID NO: 8)

WY14 (Pseudomonas sp. deposited as NRRL-B67483)
TACCGTCCCCCCGAAGGTTAGACTAGCTACTTCTGGTGCAACCCACTCCCATGGTGTGACGGGCGGTGTGTACAAGGCCC
GGGAACGTATTCACCGCGACATTCTGATTCGCGATTACTAGCGATTCCGACTTCACGCAGTCGAGTTGCAGACTGCGATC
CGGACTACGATCGGTTTTATGGGATTAGCTCCACCTCGCGGCTTGGCAACCCTCTGTACCGACCATTGTAGCACGTGTGT
AGCCCAGGCCGTAAGGGCCATGATGACTTGACGTCATCCCCACCTTCCTCCGGTTTGTCACCGGCAGTCTCCTTAGAGTG
CCCACCATAACGTGCTGGTAACTAAGGACAAGGGTTGCGCTCGTTACGGGACTTAACCCAACATCTCACGACACGAGCTG
ACGACAGCCATGCAGCACCTGTCTCAGTGTTCCCGAAGGCACCAAACCATCTCTGGTAAGTTCACTGGATGTCAAGGCCT
GGTAAGGTTCTTCGCGTTGCTTCGAATTAAACCACATGCTCCACCGCTTGTGCGGGCCCCCGTCAATTCATTTGAGTTTT
AACCTTGCGGCCGTACTCCCCAGGCGGTCAACTTAATGCGTTAGCTGCGCCACTAAAATCTCAAGGATTCCAACGGCTAG
TTGACATCGTTTACGGCGTGGACTACCAGGGTATCTAATCCTGTTTGCTCCCCACGCTTTCGCACCTCAGTGTCAGTATG
AGCCCAGGTGGTCGCCTTCGCCACTGGTGTTCCTTCCTATATCTACGCATTTCACCGCTACACAGGAAATTCCACCACCC
TCTGCCCTACTCTA (SEQ ID NO: 9)

West 9 (Pseudomonas sp. deposited as NRRL-B67307)
GTACCGTCCTCCCGAAGGTTAGACTAGCTACTTCTGGTGCAACCCACTCCCATGGTGTGACGGGCGGTGTGTACAAGGCC
CGGGAACGTATTCACCGCGACATTCTGATTCGCGATTACTAGCGATTCCGACTTCACGCAGTCGAGTTGCAGACTGCGAT
CCGGACTACGATCGGTTTTGTGGGATTAGCTCCACCTCGCGGCTTGGCAACCCTCTGTACCGACCATTGTAGCACGTGTG
TAGCCCAGGCCGTAAGGGCCATGATGACTTGACGTCATCCCCACCTTCCTCCGGTTTGTCACCGGCAGTCTCCTTAGAGT
GCCCACCATAACGTGCTGGTAACTAAGGACAAGGGTTGCGCTCGTTACGGGACTTAACCCAACATCTCACGACACGAGCT
GACGACAGCCATGCAGCACCTGTCTCAATGCTCCCGAAGGCACCAATCCATCTCTGGAAAGTTCACTTGGATGTCAAGGCC
TGGTAAGGTTCTTCGCGTTGCTTCGAATTAAACCACATGCTCCACCGCTTGTGCGGGCCCCCGTCAATTCATTTGAGTTT
TAACCTTGCGGCCGTACTCCCCAGGCGGTCAACTTAATGCGTTAGCTGCGCCACTAAAATCTCAAGGATTCCAACGGCTA
GTTGACATCGTTTACGGCGTGGACTACCAGGGTATCTAATCCTGTTTGCTCCCCACGCTTTCGCACCTCAGTGTCAGTAT
GAGCCCAGGTGGTCGCCTTCGCCACTGGTGTTCCTTCCTATATCTACGCATTTCACCGCTACACAGGAAATTCCACCACC
CTCTGCCCTACTCTAGCTTGCCAGTTTTGGATGCAGTTCCCAGGTTGAGCCCGGGGATTTCACATCCAACTTAACAAACC
ACCTACGCGCGCTTTACGCCCAGTAATTCCGATTAACGCTTGCACCCTCTGTATTACCGCGGCTGCTGGCACAGAGTTAG
CCGGTGCTTATTCTGTCGGTAACGTCAAAACACTAACGTATTAGGTTAATGCCCTTCCTCCCAACTTAAAGTGCTTTACA
ATCCGAAGACCTTCTTCACACGCGGCATGGCTGGATCAGGCTTTCGCCCATTGTCCAATATTCCCCACTGCTGCCTCCCG
TAGGAGTCTGGACCGTGTCTCAGTTCCAGTGTGACTGATCATCCTCTCAGACCAGTTACGGATCGTCGCCTTGGTGAGCC
ATTACCTCACCAACTAGCTAATCCGACCTAGGCTCATCTGATAGCGTGAGGTCCGAAGATCCCCACTTTCTCCCGTAGG
ACGTATGCGGTATTAGCGTCCCTTTCGAGACGTTGTCCCCACTACCAGGCAGATTCCTAGGCATTACTCACCCGTCCGC
CGCTGAATCAGGGAGCAAGCTCCCTCATCCGTCGACTGCA (SEQ ID NO: 10)

Microbacterium B2 (Microbacterium oxydans deposited as NRRL-B67470)
AGTCGAACGAGTGAACACGGAGCTTGCTCTGTGAGGATCAGTGGCGAACGGGTGAGTAACACGTGAGCAACCTGCCCCTG
ACTCTGGGATAAGCGCTGGAAACGGCGTCTAATACTGGATATGTGACGTGACCGCATGGTCTGCGTCTGGAAAGAATTTC
GGTTGGGGATGGGCTCGCGGCCTATCAGCTTGTTGGTGAGGTAATGGCTCACCAAGGCGTCGACGGGTAGCCGGCCTGAG TABLE 6-continued Exemplary partial 16S rDNA and SEQ ID NOS: for strains described herein AGGGTGACCGGCCACACTGGGACTGAGACACGGCCCAGACTCCTACGGGAGGCAGCAGTGGGGAATATTGCACAATGGGC
GCAAGCCTGATGCAGCAACGCCGCGTGAGGGACGACGGCCTTCGGGTTGTAAACCTCTTTTAGCAGGGAAGAAGCGAAAG
TGACGGTACCTGCAGAAAAAGCGCCGGCTAACTACGTGCCAGCAGCCGCGGTAATACGTAGGGCGCAAGCGTTATCCGGA
ATTATTGGGCGTAAAGAGCTCGTAGGCGGTTTGTCGCGTCTGCTGTGAAATCCGGAGGCTCAACCTCCGGCCTGCAGTGG
GTACGGGCAGACTAGAGTGCGGTAGGGGAGATTGGAATTCCTGGTGTAGCGGTGGAATGCGCAGATATCAGGAGGAACAC
CGATGGCGAAGGCAGATCTCTGGGCCGTAACTGACGCTGAGGAGCGAAAGGTGGGGAGCAACAGGCTTAGATACCCTGGT
AGTCCACCCCGTAACGTTGGGAACTAGTTGTGGGGTCCATTCCACGGATTCCGTGACGCAGCTAACGCATTAAGTTCCCC
GCCTGGGGAGTACGGCCGCAAGGCTAAAACTCAAAGGAATTGACGGGGACCCGCACAAGCGGCGGAGCATGCGGATTAAT
TCGATGCAACGCGAAGAACCTTACCAAGGCTTGACATATACGAGAACGGGCCAGAAATGGTCAACTCTTTGGACACTCGT
AAACAGGTGGTGCATGGTTGTCGTCAGCTCGTGTCGTGAGATGTTGGGTTAAGTCCCGCAACGAGCGCAACCCTCGTTCT
ATGTTGCCAGCACGTAATGGTGGGAACTCATGGGATACTGCCGGGGTCAACTCGGAGGAAGGTGGGGATGACGTCAAATC
ATCATGCCCCTTATGTCTTGGGCTTCACGCATGCTACAATGGCCGGTACAAAGGGCTGCAATACCGCGAGGTGGAGCGAA
TCCCAAAAAGCCGGTCCCAGTTCGGATTGAGGTCTGCAACTCGACCTCATGAAGTCGGAGTCGCTAGTAATCGCAGATCA
GCAACGCTGCGGTGAATACGTTCCCGGGTCTTGTACACACCGCCCGTCAAGTCATGAAAGTCGGTAACACCTGAAGCCGG
TGGCCTAACTTTTTGGAGGGAGCCGTCGAAGGTGGG (SEQ ID NO: 11)

WY9y (Enterobacter sp. deposited as NRRL-B67485)
GCCAGCGGTTAGGCCGGGACCTCAAAGGAGACTGCCAGTGATAAACTGGAGGAAGGTGGGGATGACGTCAAGTCATCATG
GCCCTTACGACCAGGGCTACACAGTGCTACAATGGCGCATACAAAGAGAAGCGATCTCGCGAGAGCCAGCGGACCTCATA
AAGTGCGTCGTAGTCCGGATTGGAGTCTGCAACTCGACTCCATGAAGTCGGAATCGCTAGTAATCGTGAATCAGAATGTC
ACGGTGAATACGTTCCCGGGCCTTGTACACACCGCCCGTCACACCATGGGAGTGGGTTGCAAAAGAAGT
(SEQ ID NO: 12)

Sandy Y7w (Pseudomonas sp. deposited as NRRL-B67895)
TGCCAGCGGGTAATGCCGGGAACTCAAAGGAGACTGCCGGTGATAAACCGGAGGAAGGTGGGGATGACGTCAAGTCATCA
TGGCCCTTACGGCCAGGGCTACACACGTGCTACAATGGCGCATACAAAGAGAAGCGACCTCGCGAGAGCAAGCGGACCTC
ATAAAGTGCGTCGTAGTCCGGATCGGAGTCTGCAACTCGACTCCGTGAAGTCGGAATCGCTAGTAATCGTAGATCAGAAT
GCTACGGTGAATACGTTCCCGGGCCTTGTACACACCGCCCGTCACACCATGGGAGTGGGTTGCAAAAGAAG
(SEQ ID NO: 13)

RiLB4 (Pantoea sp. deposited as NRRL-B67897)
CTCGTGTTGTGAAATGTTGGGTTAAGTCCCGCAACGAGCGCAACCCTTATCCTTTGTTGCCAGCGATTCGGTCGGGAACT
CAAAGGAGACTGCCGGTGATAAACCGGAGGAAGGTGGGGATGACGTCAAGTCATCATGGCCCTTACGAGTAGGGCTACAC
ACGTGCTACAATGGCGCATACAAAGAGAAGCGACCTCGCGAGAGCAAGCGGACCTCACAAAGTGCGTCGTAGTCCGGATC
GGAGTCTGCAACTCGACTCCGTGAAGTCGGAATCGCTAGTAATCGTGGATCAGAATGCCACGGTGAATACGTTCCCGGGC
CTTGTACACACCGCCCGTCACACCATGGGAGTGGGTTGCAAAAGAAGTAGGTAGCTTAACCTT (SEQ ID NO: 14)

SY1 (Pseudomonas sp. deposited as NRRL-B67481)
CCTTGCGCTATCAGATGAGCCTAGGTCGGATTAGCTAGTTGGTGAGGTAATGGCTCACCAAGGCGACGATCCGTAACTGG
TCTGAGAGGATGATCAGTCACACTGGAACTGAGACACGGTCCAGACTCCTACGGGAGGCAGCAGTGGGGAATATTGGACA
ATGGGCGAAAGCCTGATCCAGCCATGCCGCGTGTGTGAAGAAGGTCTTCGGATTGTAAAGCACTTTAAGGTGGGAGGAAG
GGTTGTAGATTAATACTCTGCAATTTTGACGTTACCGCCAGAATAGCACCGGCTAACTCTGTGCCAGCAGCCGCGGTAAT
ACAGAGGGTGCAAGCGTTAATCGGAATTACTGGGCGTAAAGCGCGCGTAGGTGGTTTGTTAAGTCGGATGTGAAATCCCC
GGGCTCAACCTGGGAACTGCATCCGAAACTGGCAAGCTAGAGTATGGTAGAGGGTAGTGGAATTTCCTGTGTAGCGGTGA
AATGCGTAGATATAGGAAGGAACACCAGTGGCGAAGGCGACTACCTGGACTGATACTGACACTGAGGTGCGAAAGCGTGG
GGAGCAAACAGGATTAGATACCCTGGTAGTCCACGCCGTAAACGATGTCAACTAGCCGTTGGGAGCCTTGAGCTCTTAGT
GGCGCAGCTAACGCATTAAGTTGACCGCCTGGGGAGTACGGCCGCAAGGTTAAAACTCAAATGAATTGACGGGGGCCCGC
ACAAGCGGTGGAGCATGTGGTTTAATTCGAAGCAACGCGAAGAACCTTACCAGGCCTTGACATCCAATGAACTTTCCAGA
GATGGATTGGTGCCTTCGGGAACATTGAGACAGGTGCTGCATGGCTGTCGTCAGCTCGTGTCGTGAGATGTTGGGTTAAG
TCCCGTAACGAGCGCAACCCTTGTCCTTAGTTACCAGCACGTTATGGTGGGCACTCTAAGGAGACTGCCGGTGACAAACC
GGAGGAAGGTGGGGATGACGTCAAGTCATCATGGCCCTTACGGCCTGGGCTACACACGTGCTACAATGGTCGGTACAGAG
GGTTGCCAAGCCGCGAGGTGGAGCTAATCTCACAAAACCGATCGTAGTCCGGATCGCAGTCTGCAACTCGACTGCGTGAA
GTCGGAATCGCTAGTAATCGCGAATCAGAATGTCGCGGTGAATACGTTCCCGGGCCTTGTACACACCGCCCGTCACACCA
TGGGAGTGGGTTGCACCAGAAGTAGCTAGTCTAACCTTCGGGAGGAC (SEQ ID NO: 15)

SY5 (Pseudomonas sp. deposited as NRRL-B67482)
AGCTCCACCTCGCGGCTTGGCAACCCTCTGTACCGACCATTGTAGCACGTGTGTAGCCCAGGCCGTAAGGGCCATGATGA
CTTGACGTCATCCCCACCTTCCTCCGGTTTGTCACCGGCAGTCTCCTTAGAGTGCCCACCATAACGTGCTGGTAACTAAG
GACAAGGGTTGCGCTCGTTACGGGACTTAACCCAACATCTCACGACACGAGCTGACGACAGCCATGCAGCACCTGTCTCA
ATGTTCCCGAAGGCACCAATCCATCTCTGGAAAGTTCATTGGATGTCAAGGCCTGGTAAGGTTCTTCGCGTTGCTTCGAA
TTAAACCACATGCTCCACCGCTTGTGCGGGCCCCCGTCAATTCATTTGAGTTTTAACCTTGCGGCCGTACTCCCCAGGCG
GTCAACTTAATGCGTTAGCTGCGCCACTAAGAGCTCAAGGCTCCCAACGGCTAGTTGACATCGTTTACGGCGTGGACTAC
CAGGGTATCTAATCCTGTTTGCTCCCCACGCTTTCGCACCTCAGTGTCAGTATCAGTCCAGGTAGTCGCCTTCGCCACTG
GTGTTCCTTCCTATATCTACGCATTTCACCGCTACACAGGAAATTCCACTACCCTCTACCATACTCTAGCTTGCCAGTTT
CGGATGCAGTTCCCAGGTTGAGCCCGGGGA (SEQ ID NO: 16)

Endophytic Nature of Seed-Associated Bacteria

We closely examined the properties of several endophytic bacterial species, including *Pseudomonas fluorescens* Sandy LB4, *Pseudomonas* sp. West 9 and SY1 strains isolated from invasive *Phragmites*. In our in vitro assay using axenic Bermuda grass seedlings, we showed that on germination of seeds both bacteria colonize the root meristem and enter into meristematic cells. In the process of becoming intracellular the bacteria lose their cell walls and their rod shapes to become spherical L-form bacteria. As the root meristem proliferates the intracellular bacteria become distributed in most or all cells that make up the root. Intracellular bacteria are visible early on in young differentiating root cells as small spherical aniline blue staining structures. The use of DAB to stain for $H_2O_2$ shows that the intracellular bacteria are generally surrounded by $H_2O_2$ evident as red or brown staining. $H_2O_2$ is likely produced by the host plant as a mechanism to control the intracellular bacterial endophytes.

As tissues of the root, including root hairs become older the intracellular bacteria swell and their cytoplasmic contents disappear. Presence of $H_2O_2$ around intracellular bacteria suggests that the disappearance of bacteria is due to their degradation by the host cells through oxidation. In more mature root tissues all evidence of the intracellular bacteria completely disappears from plant cells. Bacterial cells that do not enter the root tip cells do not appear to elicit a strong reactive oxygen response and may not be degraded; instead they likely remain as intercellular endophytes in the mature root tissues.

Degradation of Endophytic Microbes as a Nutritional Source

Degradation of microbes in or on roots was proposed to be a mechanism of transfer of nutrients from microbes to plant (Paungfoo-Lonhienne et al., 2010; White et al., 2012; Beltran et al., 2015). Paungfoo-Lonhienne et al. (2014) denominated the microbe consumption process 'rhizophagy' because roots consumed microbes. For a mechanism like rhizophagy to provide substantial nutrients to plants the microbes must obtain their nutrients from outside roots, then enter roots and release their nutrients to the plant tissues. We have experimental evidence that in the case of the *Pseudomonas* endophytes of *Phragmites* the bacteria move from plant out into the soil and perhaps may return to recolonize the plant root meristem. If colonization of roots by the soil bacteria is occurring with any regularity a constant flow of nutrients from soil reserves to the plant may be occurring. In previous research we hypothesized that microbes may aid plants by scavenging organic or inorganic nitrogen (White et al., 2015; Soares et al., 2016a). However, all of the bacteria we isolated from *Phragmites* seeds showed the capacity to solubilize phosphate when grown on Pikovskayas agar. Further, *Pseudomonas fluorescens* and other fluorescent pseudomonads are known to secrete fluorescent siderophores called pyoverdines that actively bind iron (Visca, Imperi and Lamont, 2006). We confirmed that Sandy LB4 secreted a fluorescent pigment that fluoresced brightly in culture and that several other strains from *Phragmites* seeds (Table 1) fluoresced lightly in culture when viewed under an ultraviolet light, suggesting that several of our isolates possess the siderophores. Sandy LB4 was also shown to produce a secreted protease (Table 1) that might enable it to degrade microbial proteins present around roots and thus acquire organic nitrogen (White et al., 2015). The capacity of the motile pseudomonads to actively move out into the soil and obtain iron and solubilize and absorb phosphorus and nitrogenous nutrients could enable the pseudomonads to provide critical nutrients to *Phragmites* to fuel its rapid growth. The endophytic pseudomonads could thus function as nutrient scavengers for their *Phragmites* seedlings (Zolg and Ottow, 1975).

Intracellular Endophytes as Elicitors of Reactive Oxygen

Bacterial endophytes that internally colonize root meristems and increase occurrence of reactive oxygen in the young differentiating tissues of the root may trigger the host to express oxidative stress resistance features to make the host more resistant to the internal oxidations. In a study of fungal endophytes in grasses it has been shown that endophytes increase the oxidative stress resistance in the host (White and Torres, 2009; Hamilton and Bauerle, 2012; Hamilton et al., 2012).

Growth Promotion

Using several species to test for growth promotion capacity of the *Phragmites* endophytes described herein, (e.g., *P. fluorescens* Sandy LB4, *Pseudomonas* sp. West 9, *Microbacterium oxydans* B2 and SY1) and another bacterium, *Bosea thiooxidans* TBN from the distant family Polygonaceae, we found that several *Phragmites* isolates increased growth of grass compared to the non-inoculated treatment (Table 2A and Table 2B); while the bacterium *Bosea thioxidans* TBN partially colonized grass seedlings and triggered root hair development but did not increase grass shoot or root growth in the soil experiment. We interpret that the *Phragmites* endophytes are compatible with the test grasses we used, but *Bosea thioxidans* TBN is only partially compatible with the grasses, incompletely colonizing root hairs and failing to increase growth of the grass host in experiments.

In an experiment where we inoculated rice seeds with Sandy LB4, seedlings bearing the bacterium showed significantly more shoot growth compared to seedlings without the bacteria. Roots were also slightly longer in bacterial treated seedlings. It was also notable that roots bearing bacteria showed greater adherence of soil particles to roots after extraction from the soil. This indicates that the presence of the bacterium may affect the physical relationship of the plant root to the soil matrix around roots. The bacterium could be increasing extraction of nutrients from soil, which could account for the increased growth of seedlings when the bacterium is present.

Effects on Seedling Development

The effects of Sandy LB4 on *Poa annua* seedling growth were seen very early in development, including a very slightly increased germination rate and greater root branching (Table 4).

Suppression of Soil Borne Disease

In co-culture experiments we demonstrated that Sandy LB4 and West 9 produced unknown antifungal substances that inhibited *Sclerotinia homeocarpa* and *Fusarium oxysporum*, while *M. oxydans* B2 did not appear to produce antifungal substances. In an experiment to assess protection from damping off disease caused by *Fusarium oxysporum* (Table 4) we showed that Sandy LB4, West 9 and *M. oxydans* B2 reduced damping off in seedlings when compared to controls inoculate with the pathogen; however Sandy LB4 was the most effective at reducing damping off. *Microbacterium oxydans* B2 was the least effective at reducing damping off disease.

In this same experiment we showed that the two pseudomonads originally inoculated onto seeds moved into the soil for some distance away from seedlings, suppressing mycelial growth in and on the surface of the soil. While *M. oxydans* B2 also moved out into the soil, it did not have any mycelial growth suppression effects and fungi grew readily over the surface of the soil in these treatments.

Some other *Pseudomonas* spp. that have been shown to be effective in biological control of diseases have been found to produce antifungal metabolites, including pyrrolnitrin, phenazines, pyoluteorin, hydrogen cyanide, etc. (Ligon et al., 2000).

Endophyte Inhibition of Competitor Species

Through a series of experiments using *Phragmites* bacteria to inoculate dandelion (*Taraxacum officionale*) and curly dock (*Rumex crispus*) we showed that the strain Sandy LB4, whether alone or in mixtures of bacteria, substantially increased mortality rates of dandelion seedlings (Table 5) and in general reduced growth and vigor in both weed species. One of the frequent features of *Pseudomonas fluorescens* is the production of hydrogen cyanide (HCN). HCN combines with cytochrome oxidase and prevents aerobic respiration. Perhaps differential susceptibility of the weeds and the grasses to HCN or other pseudomonad metabolite could be responsible for the inhibition of weed seedling growth and increased mortality. Differing sensitivity to HCN was previously suggested by Zeller, Brandle and Schmid (2007) to explain differing reactions of host and non-host species to *Pseudomonas* rhizobacteria. In this respect it is notable that many grasses secrete significant amounts of reactive oxygen ($H_2O_2$) from roots (White et al., 2012). $H_2O_2$ rapidly degrades HCN to form carbonate and ammonium ions (Yeddou et al., 2010). High production of hydrogen peroxide in grass roots could detoxify any HCN but also produce ammonia that could be absorbed and used to support plant growth. We did not see abundant $H_2O_2$ production in the roots of seedlings of either dandelion or curly dock.

Another possible mechanism to explain differential responses of host and non-host seedlings was evident when seedling roots were stained using DAB to visualize bacteria in roots. In grass roots bacteria remained as small discrete spherical bodies, likely flowing in the cytoplasm with the normal cyclosis. However, the bacteria in the non-host species appeared to form large clusters that appeared to occlude the root hairs, likely blocking normal cyclosis in the root hairs. Differential sensitivity to HCN or physical occlusion of absorptive root hairs or other structural issues may be responsible for the different responses of host grasses and non-host dandelion and curly dock seedlings to Sandy LB4.

Figure 10:
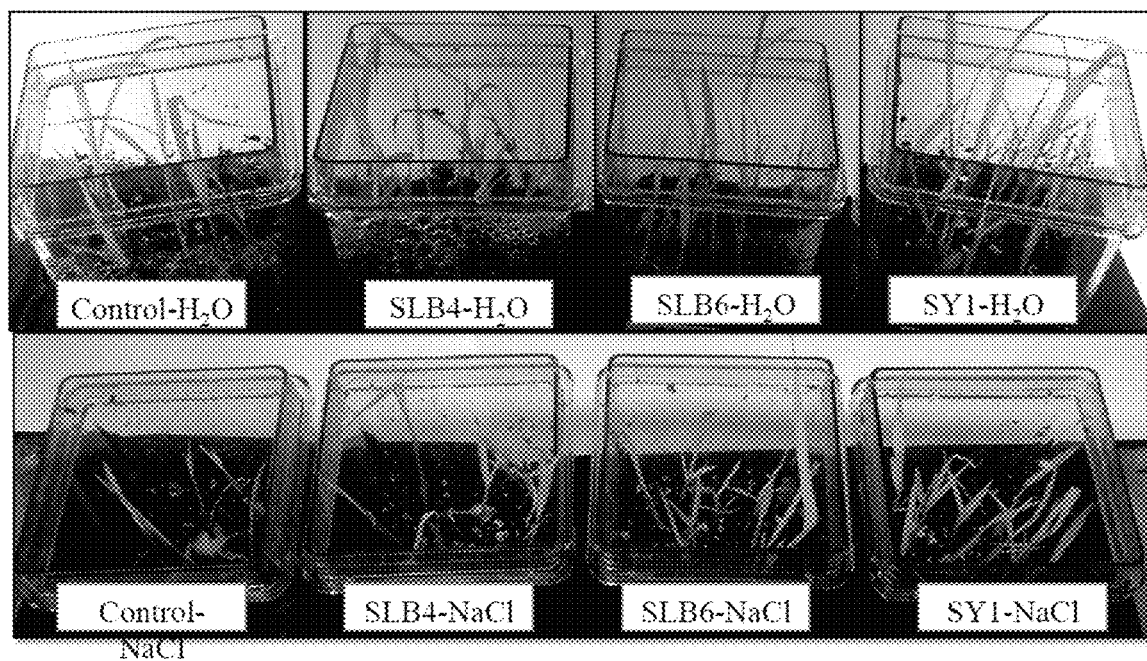
FIG. 10. Exemplary salt stress experiments in magenta boxes demonstrating that Sandy LB4, Sandy LB6 and SY1 are effective to increase salt stress tolerance in rice and Bermuda grass (*Cynodon dactylon*).

Regardless of the mechanism of inhibition the presence of some endophytes in *Phragmites* that show capability to inhibit competitor plants could provide a mechanism by which *Phragmites* excludes competitor species from its stands. The allelopathic exclusion of plants from *Phragmites* stands has been observed and previously attributed to secreted chemical inhibitors such as gallic acid (Weidenhamer et al., 2013) and phytotoxicity of *Phragmites* residues (Uddin et al., 2014). It is possible that some of the allelopathic exclusion of competitors is a function of the growth promotional pseudomonads that are endophytic in plants and likely move out into soils colonizing and inhibiting competitor plant species that are not adapted to them.
Endophytes Increase Tolerance to Salt Stress As shown in FIG. 10, each of Sandy LB4, Sandy LB6 and SY1 demonstrably increase resistance to salt stress in rice in magenta box experiments.

CONCLUSIONS

It is clear from our studies that *Phragmites* seeds carry pseudomonads that may stimulate growth and increase nutrients available to the grass, but may also inhibit soil borne fungi, suppress diseases and inhibit competitor weed species in heterologous species. The pseudomonad symbionts of *Phragmites* appear to be diverse, multifunctional and appear to increase the competitive capacity of the host.

REFERENCES

Beltran-Garcia M, White J F, Prado F M, Prieto K R, Yamaguchi L F, Torres M S, Kato M J, Madeiros H G, Di Mascio P. 2014. Nitrogen acquisition in *Agave tequilana* from degradation of endophytic bacteria. Sci Report 4: 6938. DOI:1038/srep06938

Clay K, Shearin Z R C, Bourke K A, Bickford W A, Kowalski K P. 2016. Diversity of fungal endophytes in non-native *Phragmites australis* in the Great Lakes. Biological Invasions DOI 10.1007/s10530-016-1137y.

Fischer M S, Rodriguez R J. 2013. Fungal endophytes of invasive *Phragmites australis* populations vary in species composition and fungicide susceptibility. Symbiosis 61: 55-62.

Godlewski M, Adamczyk B. 2007. The ability of plants to secrete proteases by roots. Plant Physiol Biochem 45: 657-664.

Hamilton C E, Bauerle T L. 2012. A new currency for mutualism? Fungal endophytes alter antioxidant activity in hosts responding to drought. Fungal Divers 54: 39-49.

Hamilton C E, Gundel P E, Helander M, Saikkonen K. 2012. Endophytic mediation of reactive oxygen species and antioxidant activity in plants: a review. Fungal Divers 54: 1-10.

Kloepper J W, Ryu C M, Zhang S. 2004. Induced systemic resistance and promotion of plant growth by *Bacillus* spp. Phytopathology 94: 1259-1266.

Kowalski K P, Bacon C, Bickford W, Braun H, Clay K et al. 2015. Advancing the science of microbial symbiosis to support invasive species management: a case study on *Phragmites* in the great lakes. Fronteirs in Microbiology 6: 1-14.

Ligon J M, Hill D S, Hammer P E, Torkewitz N R, Hoffman D, Kempf H-J, van Pee K.-H. 2000. Natural products with antifungal activity from *Pseudomonas* biocontrol bacteria. Pest Management Science 56: 688-695.

Paungfoo-Lonhienne C, Rentsch D, Robatzek S, Webb R, Sagulenko E, Nasholm T, Schmidt S, Lonhienne T. 2010. Turning the table: plants consume microbes as a source of nutrients. *PLOS One* 5(7): e11915.

Paungfoo-Lonhienne C, Schmidt S, Webb R, Lonhienne T. 2013. Rhizophagy—A New Dimension of Plant—Microbe Interactions, in de Briujn F J (Ed.) *Molecular Microbial Ecology of the Rhizosphere*. DOI: 10.1002/9781118297674.ch115.

Rodriguez R K, Henson J, van Volkenburgh E, Hoy M, Wright L, Beckwith F, Kim Y-O, Redman R S. 2008. Stress tolerance in plants via habitat-adapted symbiosis. ISME J. 2(4): 404-416.

Schulz B, Boyle C. 2006, What are endophytes? Pp 1-10, in Scultz B, Boyle C, Sieber T (ed) Microbial Root Endophytes, Springer-Verlag, Berlin.

Sharma S B, Sayyed R Z, Trivedi M H, Gobi T A. 2013. Phosphate solubilizing microbes: sustainable approach for managing phosphorus deficiency in agricultural soils. SpringerPlus 2: 587.

Soares M A, Li H Y, Kowalski K P, Bergen M, Torres M S, White J F. 2016a. Functional role of bacteria from invasive *Phragmites australis* in promotion of host growth. Microbial Ecology DOI: 10.1007/s00248-016-0793-x Soares M A, Li H Y, Kowalski K P, Bergen M, Torres M S, White J F. 2016b. Evaluation of the functional roles of fungal endophytes of *Phragmites australis* from high and low saline sites. Biological Invasions DOI 10.1007/s10530-016-1160-z.

Stone J K, Bacon C W, White J W. 2000. An overview of endophytic microbes: endophytism defined. Pp 3-30, In: Bacon C W, White J F (ed) Microbial Endophytes Marcel-Dekker, New York.

Uddin M N, Robinson R W, Caridi D, Harun A Y. 2014. Is phytotoxity of *Phragmites australis* residue influenced by decomposition condition, time and density? Marine and Freshwater Research 65: 505-516.

Visca P, Imperi F, Lamont I L. 2006. Pyoverdine siderophores: from biogenesis to biosignificance. Trends in Microbiology 15: 22-30.

Weidenhamer J D, Li M, Allman J, Bergosh R G, Posner M. 2013. Evidence does not support a role for gallic acid in *Phragmites australis* invasion success. J Chem Ecol 39: 323-332.

White J F, Chen Q, Torres M S, Mattera R, Irizarry I, Tadych M, Bergen M. 2015. Collaboration between grass seedlings and rhizobacteria to scavenge organic nitrogen in soils. AoB Plants January/2015. DOI: 10.1093/aobpla/plu093

White J F, Crawford H, Torres M S, Mattera R, Irizarry I, Bergen M S. 2012. A proposed mechanism for nitrogen acquisition by grass seedlings through oxidation of symbiotic bacteria. Symbiosis 57: 61-171. DOI:10.1007/s13199-012-01.

White J F, Torres M S. 2009. Is plant endophyte-mediated defensive mutualism the result of oxidative stress protection? Physiol Plant 138(4): 440-446. DOI: 10.1111/j.1399-3054.2009.01332

White J F, Torres M S, Somu M P, Johnson H, Irizarry I, Chen Q, Zhang N, Walsh E, Tadych M, Bergen M. 2014. Hydrogen peroxide staining to visualize intracellular bacterial infections of seedling root cells. Microscopy Research and Technique. May/2014; DOI: 10.1002/jemt.22375

Yeddou A R, Nadjemi B, Halet F, Ould-Dris A, Capart R. 2010. Removal of cyanide in aqueous solution by oxidation with hydrogen peroxide in presence of activated carbon prepared from olive stones. Minerals Engineering 23: 32-39.

Zeller S, Brandl H, Schmid B. 2007. Host-plant selectivity of rhizobacteria in crop/weed model system. Plos ONE 2(9): e846.DOI:10.1371/journal.pone.0000846.

Zolg W, Ottow J C G (1975) *Pseudomonas glathei* sp. nov. a new nitrogen scavenging rod isolated from acid lateritic relicts in Germany. Z Allg Mikrobiol 15:287-299

Example II

Application of Combinations of Heterologous Endophytic Bacteria to Improve Agronomic Traits As described in the previous example, the endophytic bacteria listed in Table 1 can be used alone or in combination to confer beneficial phenotypic changes to host plants. These changes include one or more of an increase in root growth promotion, shoot growth promotion, resistance to salt stress, competition with undesirable plant species and resistance to fungus in a plant produced from the seed, as compared to a reference plant which is not treated with the inventive bacterial combination. The bacteria can act synergistically in combination or their effects may be additive in achieving the advantages set forth above. Such combinations can include 1, 2, 3, 4, 5, 6, 7, 8, 9, 10 or all of the strains listed in Table 1. The strains may be present in differing amounts or ratios, e.g., 1:1, 1:2, 1:3, 1:4, 1:2:1, 1:5:1, etc. Exemplary combinations include, without limitation: protease positive strains such as Sandy LB4 or Sandy LB6 in combination of antifungal (protease negative) strains SY1 or SY5. This combination provides increased functionality to the plant microbe combination. Protease positive strains WY6 or WY14 in combination with protease negative strain WY9y should also act to enhance plant growth. The phosphatase negative strain *Microbacterium oxydans* B2 combined with phosphatase positive strains Sandy LB4 or Sandy LB6 should enhance phosphate scavenging capability as well as other processes effective to increase of plant growth.

The combined bacteria may be formulated to facilitate administration to target plants of interest, using methods described herein above. They may be lyophilized, and optionally formulated into synthetic alginate beads for distribution into soil. Alternatively, they can be formulated as an aerosol for spraying on areas to be treated. Such methods are known to those of skill in the art of plant and crop propagation.

The formulations described above can also be added to certain fertilizer compositions, such as the controlled release fertilizer composition described in U.S. Pat. No. 9,266,787. Such fertilizer compositions can optionally comprise one or more reagents selected from urea, ammonia, ammonium nitrate, ammonium sulfate, calcium nitrate, diammonium phosphate, monoammonium phosphate, potassium nitrate and sodium nitrate. monopotassium phosphate, dipotassium phosphate, tetrapotassium pyrophosphate, and potassium metaphosphate and optionally a macronutrient selected from the group consisting of sulfur, calcium and magnesium and/or micronutrients including boron, copper, iron, manganese, molybdenum and zinc provided that such reagent does not interfere with the growth promoting action of the endophytic bacteria described herein.

These aforementioned formulations and compositions can further comprise a dispersing agent, such as those disclosed in U.S. Pat. No. 8,241,387.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A synthetic combination comprising at least one purified bacterial population in association with a seed of a turf and forage grass, wherein the purified bacterial population comprises a seed bacterial endophyte, SY1 deposited as NRRL-B67481, that is heterologously disposed to the turf or forage grass seed, wherein the seed bacterial endophyte is present in the synthetic combination at a concentration of at least $10^3$ CFU/seed on the surface of a seed, and in an amount effective to increase one or more of root growth promotion, shoot growth promotion, resistance to salt stress, competition with undesirable plant species and increase resistance to fungus in a plant produced from the seed, as compared to a reference plant grown under the same conditions.

2. The synthetic combination of claim 1, wherein said bacteria are lyophilized.

3. The synthetic combination of claim 1, wherein said bacteria are encapsulated in an alginate bead formulation.

4. The synthetic combination of claim 1, wherein said bacteria are present in a seed ball.

5. The synthetic combination of claim 1, wherein said combination includes at least one of Sandy LB4 deposited as NRRL B-67308, and *Microbacterium oxydans* B2 deposited as NRRL-B67470, wherein said seed is a rice seed or a grass seed.

6. The synthetic combination of claim 1, wherein said combination further comprises at least one of Sandy LB6 deposited as NRRL B-67484 and West 9 deposited as NRRL B67307 and wherein said seed is a grass seed from a grass selected from *Agrostis* spp., *Poa* spp., *Festuca* spp., *Lolium* spp., *Cynodon* spp., *Zoysia* spp., *Koleria* spp., and *Danthonia* spp.

7. The synthetic combination of claim 5, further comprising WY14 deposited as NRRL-B-67483 wherein said seed is a rice seed or a grass seed.

8. A method of reducing undesirable weed growth in soils comprising turf and forage grasses, comprising drenching or treating the soil with one or more biologically pure *Pseudomonas* spp. endophyte strains wherein said strains reduce weed growth relative to weed growth observed in untreated soil, wherein said one or more *Pseudomonas* spp. is SY1 deposited as NRRL B-67481.

9. The method of claim 8, further comprising one or more biologically pure endophyte strains Sandy LB4 deposited as NRRL B-67308 and/or *Microbacterium oxydans* B2 deposited as NRRL-B67470, and/or WY6 comprising SEQ ID NO: 7, and/or WY14 deposited as NRRL-B-67483 wherein said strains are obtained from *Phragmites* and said endophytes are lyophilized.

10. The synthetic combination of claim 1, comprising one or more bacteria selected from the group consisting of
   i) protease negative strain West 9 deposited as NRRL B67307;
   ii) phosphatase positive strain Sandy LB6 deposited as NRRL B-67484;
   iii) phosphatase positive strain WY14 deposited as NRRL-B-67483; and
   iv) strain SY5 deposited as NRRL B67482.

11. The synthetic combination of claim 10, wherein said at least one biologically pure endophyte strain is obtained from *Phragmites* and said bacteria are lyophilized.

12. The synthetic combination of claim 1 further comprising one or more of Sandy LB6 comprising SEQ ID NO: 2 deposited as NRRL B-67484, Sandy Y8 comprising SEQ ID NO: 3 and deposited under NRRL B-67896, RoY12 comprising SEQ ID NO: 6 and deposited under NRRL B-67898, RoLB13w comprising SEQ ID NO: 5 and deposited under NRRL B-67894, West 9 comprising SEQ ID NO: 10 and deposited as NRRL B-67307, RiY3 comprising SEQ ID NO: 4 and deposited under NRRL B-67893, SandyY7w comprising SEQ ID NO: 13 and deposited under NRRL B-67895, RiLB4 comprising SEQ ID NO:14 and deposited under NRRL B-67897, and SY5 comprising SEQ ID NO: 16 and deposited as NRRL B-67482.

13. A method of increasing root and shoot growth of a grass plant host, comprising inoculating the host grass or seed with the synthetic combination of claim 1, said synthetic combination being effective to increase one or more of root growth promotion, shoot growth promotion, resistance to salt stress, competition with undesirable plant species and resistance to fungus in a plant produced from the seed, as compared to a reference plant grown under the same conditions.

14. The method of claim 13, wherein the inoculated host grass exhibits suppressed growth of soil borne fungal pathogens of said host grass relative to host grasses which have not been inoculated with said synthetic combination.

15. The method of claim 13, wherein the host grass is a turf and forage grass selected from *Agrostis* spp., *Poa* spp., *Festuca* spp., *Lolium* spp., *Cynodon* spp., *Zoysia* spp., *Koleria* spp., *Paspalum* spp., *Panicum* spp., *Stenotaphrum* spp., *Eremochloa* spp. and *Danthonia* spp., *Triticum aestivum, Oryza sativa, Avena sativa, Hordeum vulgare, Panicum miliaceum, Eleusine coracana, Sorghum bicolor, Pennisetum glaucum, Setaria italica, Zea maydis, Agrostis* spp., *Poa* spp., *Festuca* spp., *Lolium* spp., *Cynodon* spp., *Zoysia* spp., *Koleria* spp., and *Danthonia* spp.

16. The method of claim 13, wherein the host grass is a food grass crop selected from *Oryza sativa, Triticum aestivum*, and *Zea maydis*.

17. The method of claim 13, wherein the host grass is a Pooideae grass.

18. The method of claim 13, wherein said synthetic combination is present in a synthetic seed ball.

19. The method of claim 13, wherein said plant host is sprayed with a liquid formulation comprising said synthetic combination.

20. The method of claim 13, wherein said synthetic combination is present in a controlled release fertilizer formulation.

21. The method of claim 13, wherein said synthetic combination comprises one or more of Sandy LB4 deposited as NRRL B-67308 and/or *Microbacterium oxydans* B2 deposited as NRRL-B67470, and/or WY6 comprising SEQ ID NO: 7, and/or WY14 deposited as NRRL-B-67483.

22. The method of claim 13, wherein said synthetic combination comprises one or more of Sandy LB6 comprising SEQ ID NO: 2 deposited as NRRL B-67484, Sandy Y8 comprising SEQ ID NO: 3 and deposited under NRRL B-67896, RoY12 comprising SEQ ID NO: 6 and deposited under NRRL B-67898, RoLB13w comprising SEQ ID NO: 5 and deposited under NRRL B-67894, West 9 comprising SEQ ID NO: 10 and deposited as NRRL B-67307, RiY3 comprising SEQ ID NO: 4 and deposited under NRRL B-67893, SandyY7w comprising SEQ ID NO: 13 and deposited under NRRL B-67895, RiLB4 comprising SEQ ID NO:14 and deposited under NRRL B-67897, and SY5 comprising SEQ ID NO: 16 and deposited as NRRL B-67482.

\* \* \* \* \*

UNITED STATES PATENT AND TRADEMARK OFFICE
CERTIFICATE OF CORRECTION

| | |
|---|---|
| PATENT NO. | : 10,721,936 B2 |
| APPLICATION NO. | : 15/657100 |
| DATED | : July 28, 2020 |
| INVENTOR(S) | : James F. White, Jr., Kurt P. Kowalski and Kathryn Kingsley |

Page 1 of 1

It is certified that error appears in the above-identified patent and that said Letters Patent is hereby corrected as shown below:

In the Specification

Left-hand column, at Line 8, before the heading "CROSS REFERENCE TO RELATED APPLICATIONS", Insert the following:
-- STATEMENT OF FEDERAL FUNDING
This invention was made with government support under NI17HMFPXXXXG024 and NI20HMFPXXXXG002 awarded by the National Institute of Food and Agriculture. The government has certain rights in the invention. --

Signed and Sealed this
Fourteenth Day of October, 2025

John A. Squires
*Director of the United States Patent and Trademark Office*